(12) United States Patent
Ramsey et al.

(10) Patent No.: US 7,932,042 B1
(45) Date of Patent: Apr. 26, 2011

(54) METHODS AND COMPOSITIONS FOR THE TREATMENT OF PSYCHOTIC DISORDERS THROUGH THE IDENTIFICATION OF THE OLANZAPINE POOR RESPONSE PREDICTOR GENETIC SIGNATURE

(75) Inventors: Timothy L. Ramsey, Shelbyville, KY (US); Bharat Mehrotra, Louisville, KY (US); Mark D. Brennan, Jeffersonville, IN (US)

(73) Assignee: Suregene, LLC, Jeffersontown, KY (US)

( * ) Notice: Subject to any disclaimer, the term of this patent is extended or adjusted under 35 U.S.C. 154(b) by 0 days.

(21) Appl. No.: 12/903,891

(22) Filed: Oct. 13, 2010

(51) Int. Cl.
*C07H 21/04* (2006.01)
*C12Q 1/68* (2006.01)

(52) U.S. Cl. ......... 435/6; 435/91.1; 435/91.2; 536/23.1; 536/24.3

(58) Field of Classification Search .................. None
See application file for complete search history.

(56) References Cited

U.S. PATENT DOCUMENTS

| | | | |
|---|---|---|---|
| 6,476,208 B1 | 11/2002 | Cohen et al. ................. 536/23.1 |
| 6,555,316 B1 | 4/2003 | Cohen et al. ...................... 435/6 |
| 7,067,627 B2 | 6/2006 | Cohen et al. ................. 530/350 |
| 7,371,811 B2 | 5/2008 | Cohen et al. ................. 530/300 |
| 7,790,396 B1 | 9/2010 | Ramsey et al. ..................... 435/6 |
| 2003/0170667 A1 | 9/2003 | Kaytes et al. ...................... 435/6 |
| 2003/0224365 A1 | 12/2003 | Wood et al. ........................ 435/6 |
| 2004/0115699 A1 | 6/2004 | Kaytes et al. ...................... 435/6 |
| 2005/0176057 A1 | 8/2005 | Bremer et al. ..................... 435/6 |
| 2005/0260667 A1 | 11/2005 | Cohen et al. ....................... 435/6 |
| 2006/0234223 A1 | 10/2006 | Darvasi et al. .................... 435/6 |
| 2007/0026402 A1 | 2/2007 | Noble et al. ....................... 435/6 |
| 2007/0031853 A1 | 2/2007 | Stanton, Jr. et al. .............. 435/6 |
| 2007/0231801 A1 | 10/2007 | Martucci et al. .................. 435/6 |
| 2008/0182268 A1 | 7/2008 | Cohen et al. ....................... 435/6 |
| 2008/0206768 A1 | 8/2008 | Arranz .............................. 435/6 |
| 2009/0075827 A1 | 3/2009 | Young et al. ....................... 506/7 |
| 2009/0281090 A1 | 11/2009 | He et al. ......................... 514/220 |
| 2010/0105062 A1 | 4/2010 | Brennan et al. ................... 435/6 |
| 2010/0131432 A1 | 5/2010 | Kennedy et al. .............. 705/500 |
| 2010/0151461 A1 | 6/2010 | Brennan ........................... 435/6 |

FOREIGN PATENT DOCUMENTS

| | | |
|---|---|---|
| WO | WO 00/22122 | 4/2000 |
| WO | WO 00/50639 | 8/2000 |
| WO | WO 01/40493 | 6/2001 |
| WO | WO 02/086147 | 10/2002 |
| WO | WO 03/020980 | 3/2003 |
| WO | WO 03/101377 | 12/2003 |
| WO | WO 2004/020580 | 3/2004 |
| WO | WO 2005/007871 | 1/2005 |
| WO | WO 2005/118848 | 12/2005 |
| WO | WO 2008/076449 | 6/2008 |
| WO | WO 2008/086579 | 7/2008 |
| WO | WO 2009/082743 | 7/2009 |
| WO | WO 2009/089120 | 7/2009 |
| WO | WO 2009/092032 | 7/2009 |
| WO | WO 2010/036353 | 4/2010 |

OTHER PUBLICATIONS

Sullivan et al. "Genomewide assocation for schizophrenia in the CATIE study: results of stage 1" Molecular Psychiatry, vol. 13, pp. 570-584, 2008.*

Mudge et al., "Genomic convergence analysis of Schizophrenia: mRNA sequencing reveals altered synaptic vesicular transport in post-mortem cerebellum," *PLoS ONE*, 3:e3625, 2008.

Reference SNP(refSNP) Cluster Report: rs7975477, Entrez SNP, Dec. 30, 2008, Retrieved from the internet, http://www.ncbi.nlm.nih.gov/projects/SNP/snp_ref.cgi?rs=7975477, Sep. 15, 2010.

Reference SNP(refSNP) Cluster Report: rs11960832, Entrez SNP, Dec. 30, 2008, Retrieved from the internet, http://www.ncbi.nlm.nih.gov/projects/SNP/snp_ref.cgi?rs=11960832, Sep. 15, 2010.

* cited by examiner

*Primary Examiner* — Jeanine A Goldberg
(74) *Attorney, Agent, or Firm* — Fulbright & Jaworski L.L.P.

(57) ABSTRACT

Methods and compositions relate to genetic markers of psychotic disorders, e.g., schizophrenia (SZ), are provided. For example, in certain aspects methods for determinations of a OPRP genetic signature are described. Furthermore, the invention provides methods and compositions involving treatment of psychotic disorders using the genetic signature.

6 Claims, 1 Drawing Sheet

METHODS AND COMPOSITIONS FOR THE TREATMENT OF PSYCHOTIC DISORDERS THROUGH THE IDENTIFICATION OF THE OLANZAPINE POOR RESPONSE PREDICTOR GENETIC SIGNATURE

This invention was made with government support under SBIR grant MH078437 awarded by National Institutes of Mental Health. The government has certain rights in the invention.

BACKGROUND OF THE INVENTION

1. Field of the Invention

The present invention relates generally to the field of psychotic disorders, such as schizophrenia. More particularly, it concerns genetic markers of antipsychotic response, for example, genes and genetic markers that influence or predict a person's likely response to antipsychotic medications.

2. Description of Related Art

Numerous drugs exist to treat psychotic disorders, such as schizophrenia (SZ), related SZ-spectrum disorders (including schizotypal personality disorder (SPD) and schizoaffective disorder (SD)), and bipolar disorders (BD). Most of these drugs fall into one of two categories, typical (first generation) and atypical (second generation).

Although head to head studies of large groups of patients, either in the acute phase or outpatient treatment, show that most atypical antipsychotic drugs are equally efficacious for positive symptoms, there are individual differences in response to specific drugs based on differences in drug pharmacology and metabolism, combined with genetic differences between patients. There are currently no proven ways to identify which antipsychotic drug is optimal for a given patient. Thus, patients switch from one drug to another when response is not considered to be adequate or side effects are intolerable. This switching of medication incurs a variety of increased costs, both economic and patient and caregiver hardship. Moreover, the limited or partial response that is often seen with antipsychotics leads to polypharmacy, where physicians prescribe two or more antipsychotic drugs plus mood stabilizers and/or antidepressants. Polypharmacy increases medication costs and significantly increases the likelihood of adverse advents and drug interactions (Stahl and Grady, 2006). On average, each patient may change medications three times for finding one that works. Additionally, the current drug have significant side-effects. This combination of side-effects and limited efficacy create a vast unmet need for selecting the optimal antipsychotic for each patient.

Pharmacogenomics, using genetic variation to predict altered response and side-effects profiles, will be important for enhanced patient care going forward. There continues to exist, therefore, a need to identify specific genetic variations that are associated with psychotic disorders such as schizophrenia.

SUMMARY OF THE INVENTION

The invention is in part based on the finding that a genetic signature, which the inventors refer to as the Olanzapine Poor Response Predictor (OPRP), is a biomarker that can be used for selecting a more appropriate antipsychotic treatment plan for that particular subject. For example, the inventors have discovered that patients that are OPRP negative respond better than patients that are OPRP positive when treated with olanzapine, and that OPRP negative patients respond better to olanzapine than to other antipsychotics. Thus, prior determination of a patient's OPRP status can aid in the development of an optimal antipsychotic treatment regimen. One aspect of the invention involves a method for obtaining genetic information about a test subject comprising (a) obtaining a biological sample comprising genetic material of a test subject, wherein the test subject is undergoing or is to undergo antipsychotic pharmacotherapy; (b) determining whether the genetic material comprises an Olanzapine Poor Response Predictor (OPRP) genetic signature, determining the Olanzapine Poor Response Predictor (OPRP) genetic signature status of the subject, wherein the OPRP genetic signature is defined as a genotype comprising a homozygous genotype for the T allele at rs11960832 and either a homozygous or heterozygous genotype for the T allele at rs7975477, to thereby obtain the genetic information.

Thus, an aspect of the invention involves determining whether genetic material of the subject comprises a ORRP genetic signature. Of course, to meet the need to transfer and store genetic information, the results of the determination will preferably be recorded and maintained in a tangible medium, such as a computer-readable disk, a solid state memory device, an optical storage device or the like, more specifically, a storage device such as a hard drive, a Compact Disk (CD) drive, a floppy disk drive, a tape drive, a random access memory (RAM), etc.

One preferred manner of obtaining the genetic signature information involves analyzing the genetic material of the subject to determine the presence or absence of the OPRP genetic signature. This can be accomplished, for example, by testing the subject's genetic material through the use of a biological sample. In certain embodiments, the methods set forth will thus involve obtaining a biological sample from the subject and testing the biological sample to identify whether an OPRP genetic signature is present. The biological sample may be any biological material that contains DNA or RNA of the subject, such as a nucleated cell source. Non-limiting examples of cell sources available in clinical practice include hair, skin, nucleated blood cells, buccal cells, any cells present in tissue obtained by biopsy or any other cell collection method. The biological sample may also be obtained from body fluids, including without limitation blood, saliva, sweat, urine, amniotic fluid (the fluid that surrounds a fetus during pregnancy), cerebrospinal fluid, feces, and tissue exudates at the site of infection or inflammation. DNA may be extracted from the biologic sample such as the cell source or body fluid using any of the numerous methods that are standard in the art.

Determining whether the genetic material exhibits an OPRP genetic signature can be by any method known to those of ordinary skill in the art, such as genotyping (e.g., SNP genotyping) or sequencing. Techniques that may be involved in this determination are well-known to those of ordinary skill in the art. Examples of such techniques include allele specific oligonucleotide hybridization, size analysis, sequencing, hybridization, 5' nuclease digestion, single-stranded conformation polymorphism analysis, allele specific hybridization, primer specific extension, and oligonucleotide ligation assays. Additional information regarding these techniques is discussed in the specification below.

For genetic signature determinations, the sequence of the extracted nucleic acid of the subject may be determined by any means known in the art, including but not limited to direct sequencing, hybridization with allele-specific oligonucleotides, allele-specific PCR, ligase-PCR, HOT cleavage, denaturing gradient gel electrophoresis (DDGE), and single-stranded conformational polymorphism (SSCP) analysis. Direct sequencing may be accomplished by any method, including without limitation chemical sequencing, using the Maxam-Gilbert method, by enzymatic sequencing, using the Sanger method; mass spectrometry sequencing; and sequencing using a chip-based technology. In particular embodiments, DNA from a subject is first subjected to amplification by polymerase chain reaction (PCR) using specific amplification primers. In some embodiments, the method further involves amplification of a nucleic acid from the biological sample. The amplification may or may not involve PCR. In some embodiments, the primers are located on a chip.

The subject can be any subject, such as a mammal. Non-limiting examples of mammals include mice, rats, rabbits, dogs, cats, sheep, goats, non-human primates (chimpanzees, baboons, monkeys), cows, horses, pigs, and humans. In specific embodiments, the subject is a human. For example, in some embodiments the human is a subject who has or is suspected to have a psychotic disorder, such as schizophrenia, schizotypal personality disorder (SPD), schizoaffective disorder (SD), or bipolar disorder (BD). The subject can be a human (e.g., a patient having, suspected to have, or at risk of, a psychotic disorder). In one embodiment, the subject is a patient having previously diagnosed a psychotic disorder (e.g., a patient suffering from early, intermediate or aggressive a psychotic disorder). In some embodiments, the subject is of Caucasian (CA) descent, i.e., has one or more ancestors who are CA. In some embodiments, the subject is of African American (AA) descent, i.e., has one or more ancestors who are AA.

Moreover, the inventors contemplate that the genetic structure and sequence, including SNP profiles, of individual subjects will at some point be widely or generally available, or will have been developed by an unrelated third party. In such instances, there will be no need to test or analyze the subject's biological material again. Instead, the genetic information will in such cases be obtained simply by analyzing the sequencing or genotyping outcome of the subject, for example, a SNP profile, a whole or partial genome sequence, etc. These outcomes can then be obtained from or reported by a sequencing or a genotyping service, a laboratory, a scientist, or any genetic test platforms.

In some further aspects, the method may further comprise reporting the determination to the subject, a health care payer, an attending clinician, a pharmacist, a pharmacy benefits manager, or any person that the determination may be of interest.

In certain embodiments, there is also provided a method for treating a human subject having or suspected of having a psychotic disorder, comprising a) selecting a subject that has been determined to have the OPRP genetic signature, defined as a genotype comprising a homozygous genotype for the T allele at rs11960832 and either a homozygous or heterozygous genotype for the T allele at rs7975477, wherein if the subject comprises the OPRP genetic signature, the subject is less likely to exhibit a favorable response to olanzapine, and treating the subject with an anti-psychotic treatment other than olanzapine; and b) selecting a subject that has been determined not to have the OPRP genetic signature, wherein if the subject does not comprise the OPRP genetic signature, the subject is more likely to exhibit a favorable response to olanzapine, and treating the subject with olanzapine.

In certain embodiments, there is also provided a method of developing a pharmacotherapeutic treatment plan for a subject having or suspected of having a psychotic disorder comprising determining the OPRP status of the patient, wherein a) if the human subject comprises the OPRP genetic signature, the subject is less likely to exhibit a favorable response to olanzapine; and b) if the subject does not comprise the OPRP genetic signature, the subject is more likely to exhibit a favorable response to olanzapine; and developing the pharmacotherapeutic treatment plan. For example, if the subject does not comprise an OPRP genetic signature, then the method may further comprise treating the subject with olanzapine. If the subject does comprise the OPRP genetic signature, then the method may further comprise treating the subject with an anti-psychotic treatment other than olanzapine, such as treating with risperidone, quetiapine, ziprasidone or perphenazine. In some embodiments, the psychotic disorder may be schizophrenia.

Certain aspects of the invention may involve a method for treating a subject having a psychotic disorder and determined not to have an OPRP genetic signature, comprising treating the subject with olanzapine. In some further aspects, the invention may include a method for treating a subject having a psychotic disorder and determined to have an OPRP genetic signature, comprising treating the subject with a non-olanzapine anti-psychotic treatment.

Certain aspects of the invention may involve a method for treating a subject comprising selecting a subject that is determined to have an OPRP genetic signature and developing an appropriate treatment plan. Other aspects of the invention may involve a method for treating a subject comprising selecting a subject that is determined not to have an OPRP genetic signature and developing an appropriate treatment plan. Prior determination of a patient's an OPRP genetic signature status may be obtained from or reported by a sequencing or a genotyping service, a laboratory, a scientist, or any genetic test platforms.

Certain aspects of the present invention also contemplate the preparation of kits or arrays for use in accordance with the present invention. Suitable kits include various reagents for use in accordance with the present invention in suitable containers and packaging materials, including tubes, vials, and shrink-wrapped and blow-molded packages. Such an array or a kit may comprise a plurality of primers or probes specific for an OPRP genetic signature. The array may be a genotyping chip. Also a tangible, computer-readable medium comprising a SNP profile of a subject may also be provided, wherein the SNP profile exhibits the presence or absence of an OPRP genetic signature.

Embodiments discussed in the context of methods and/or compositions of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWING

The following drawing forms part of the present specification and is included to further demonstrate certain aspects of the present invention. The invention may be better understood by reference to this drawing in combination with the detailed description of specific embodiments presented herein.

DESCRIPTION OF ILLUSTRATIVE EMBODIMENTS

Figure 1:
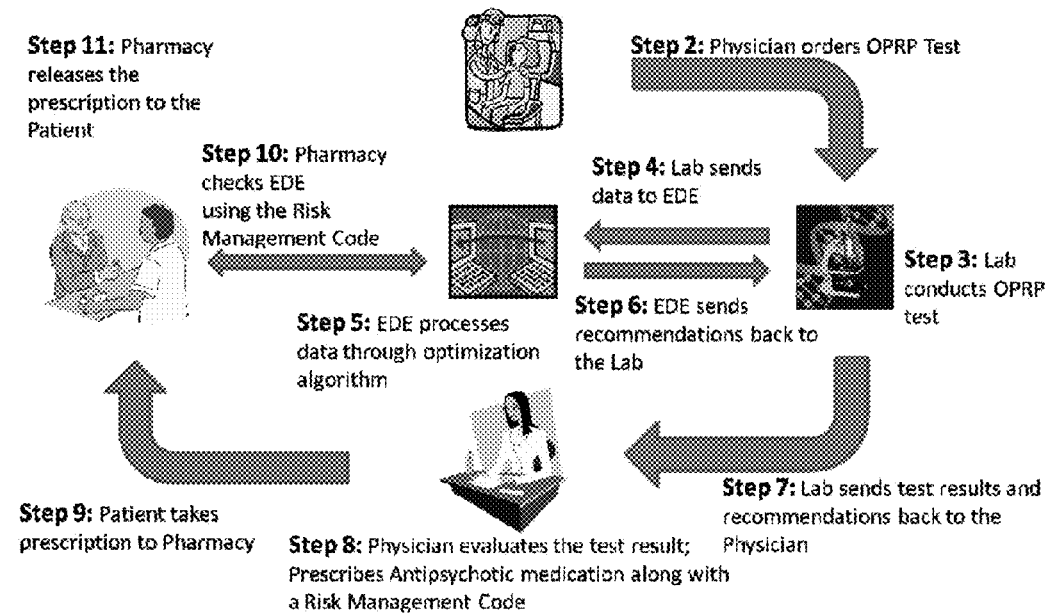
FIG. 1: An exemplary embodiment of risk management involving OPRP genetic signature determination.

Choosing the correct antipsychotic medication for patients suffering from severe neuropsychiatric illnesses is a major challenge. Fewer than one in three patients suffering from schizophrenia and related disorders will have a robust improvement in symptoms on the first antipsychotic drug prescribed. One out of three patients will be resistant to commonly used drugs. Furthermore, the metabolic side-effects of antipsychotic drugs, most commonly seen with olanzapine and clozapine, result in low compliance, with 50% of patients discontinuing drug use within 6 months of prescription, leading to relapse (return of psychosis) and hospitalization.

Therefore, methods and compositions of the present invention will help to meet this challenge by assisting physicians, patients, lab, or pharmacists with selection or recommendation of appropriate antipsychotic medication. Specifically, the present inventors have used an OPRP genetic signature for related psychotic disorders for pharmacogenomic applications, i.e., assessing the impact of genetic variation on drug response. Examples of variation in drug response include any of the following efficacy, side-effect profile, treatment maintenance and discontinuation rates, return to work status, hospitalizations, suicidality, total healthcare cost, social functioning scales, response to non-pharmacological treatments, and dose response curves. Efficacy includes but is not limited to the following definition: ≧10% decrease in Total PANSS score. Side-effect profile includes one or more of weight gain, metabolic dysfunction, lipid dysfunction, movement disorders, and extrapyramidal symptoms.

Further embodiments and advantages of the invention are described below.

I. Definitions

As defined herein, "Schizophrenia" or "SZ" includes the SZ-spectrum disorders, Schizotypal Personality Disorder (SPD) and Schizoaffective Disorder (SD), as well as Schizophrenia under the narrower, DSM-IV definition.

As used herein, a "genetic signature" is a mutually exclusive set of genotypes comprising a group of markers (e.g., polymorphisms). As used herein, the term "polymorphism" refers to the condition in which there is a variation in the DNA sequence between some members of a species. A genetic signature can consist of a variety of genetic markers, including indels (insertions or deletions of the DNA at particular locations on the chromosome); single nucleotide polymorphisms (SNPs) in which a particular nucleotide is changed; microsatellites; and minisatellites.

As used herein, a "OPRP genetic signature" refers to a genetic signature comprising homozygous genotype for the T allele at SNP marker rs11960832, i.e., rs11960832(T)/rs11960832(T) homozygosity, in combination with either a homozygous or heterozygous genotype for the T allele at marker rs7975477, i.e., rs7975477(T)/rs7975477(T) homozygosity or rs7975477(T)/rs7975477(C) heterozygosity.

The term "chromosome" as used herein refers to a gene carrier of a cell that is derived from chromatin and comprises DNA and protein components (e.g., histones). The conventional internationally recognized individual human genome chromosome numbering identification system is employed herein. The size of an individual chromosome can vary from one type to another with a given multi-chromosomal genome and from one genome to another. In the case of the human genome, the entire DNA mass of a given chromosome is usually greater than about 100,000,000 base pairs. For example, the size of the entire human genome is about $3 \times 10^9$ base pairs.

The term "gene" refers to a DNA sequence in a chromosome that codes for a product (either RNA or its translation product, a polypeptide). A gene contains a coding region and includes regions preceding and following the coding region (termed respectively "leader" and "trailer"). The coding region is comprised of a plurality of coding segments ("exons") and intervening sequences ("introns") between individual coding segments.

The term "probe" refers to an oligonucleotide. A probe can be single stranded at the time of hybridization to a target. As used herein, probes include primers, i.e., oligonucleotides that can be used to prime a reaction, e.g., a PCR reaction.

The term "label" or "label containing moiety" refers in a moiety capable of detection, such as a radioactive isotope or group containing same, and nonisotopic labels, such as enzymes, biotin, avidin, streptavidin, digoxygenin, luminescent agents, dyes, haptens, and the like. Luminescent agents, depending upon the source of exciting energy, can be classified as radioluminescent, chemiluminescent, bioluminescent, and photoluminescent (including fluorescent and phosphorescent). A probe described herein can be bound, e.g., chemically bound to label-containing moieties or can be suitable to be so bound. The probe can be directly or indirectly labeled.

The term "direct label probe" (or "directly labeled probe") refers to a nucleic acid probe whose label after hybrid formation with a target is detectable without further reactive processing of hybrid. The term "indirect label probe" (or "indirectly labeled probe") refers to a nucleic acid probe whose label after hybrid formation with a target is further reacted in subsequent processing with one or more reagents to associate therewith one or more moieties that finally result in a detectable entity.

The terms "target," "DNA target," or "DNA target region" refers to a nucleotide sequence that occurs at a specific chromosomal location. Each such sequence or portion is preferably at least partially, single stranded (e.g., denatured) at the time of hybridization. When the target nucleotide sequences are located only in a single region or fraction of a given chromosome, the term "target region" is sometimes used. Targets for hybridization can be derived from specimens which include, but are not limited to, chromosomes or regions of chromosomes in normal, diseased or malignant human cells, either interphase or at any state of meiosis or mitosis, and either extracted or derived from living or postmortem tissues, organs or fluids; germinal cells including sperm and egg cells, or cells from zygotes, fetuses, or embryos, or chorionic or amniotic cells, or cells from any other germinating body; cells grown in vitro, from either long-term or short-term culture, and either normal, immortalized or transformed;

inter- or intraspecific hybrids of different types of cells or differentiation states of these cells; individual chromosomes or portions of chromosomes, or translocated, deleted or other damaged chromosomes, isolated by any of a number of means known to those with skill in the art, including libraries of such chromosomes cloned and propagated in prokaryotic or other cloning vectors, or amplified in vitro by means well known to those with skill; or any forensic material, including but not limited to blood, or other samples.

The term "hybrid" refers to the product of a hybridization procedure between a probe and a target. The term "hybridizing conditions" has general reference to the combinations of conditions that are employable in a given hybridization procedure to produce hybrids, such conditions typically involving controlled temperature, liquid phase, and contact between a probe (or probe composition) and a target. Conveniently and preferably, at least one denaturation step precedes a step wherein a probe or probe composition is contacted with a target. Guidance for performing hybridization reactions can be found in Ausubel et al. (2003). Aqueous and nonaqueous methods are described in that reference and either can be used. Hybridization conditions referred to herein are a 50% formamide, 2×SSC wash for 10 minutes at 45° C. followed by a 2×SSC wash for 10 minutes at 37° C.

Calculations of "identity" between two sequences can be performed as follows. The sequences are aligned for optimal comparison purposes (e.g., gaps can be introduced in one or both of a first and a second nucleic acid sequence for optimal alignment and non-identical sequences can be disregarded for comparison purposes). The length of a sequence aligned for comparison purposes is at least 30%, e.g., at least 40%, 50%, 60%, 70%, 80%, 90% or 100%, of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two nucleotide sequences is determined using the GAP program in the GCG software package, using a Blossum 62 scoring matrix with a gap penalty of 12, a gap extend penalty of 4, and a frameshift gap penalty of 5.

As used herein, the term "substantially identical" is used to refer to a first nucleotide sequence that contains a sufficient number of identical nucleotides to a second nucleotide sequence such that the first and second nucleotide sequences have similar activities. Nucleotide sequences that are substantially identical are at least 80%, e.g., 85%, 90%, 95%, 97% or more, identical.

The term "nonspecific binding DNA" refers to DNA which is complementary to DNA segments of a probe, which DNA occurs in at least one other position in a genome, outside of a selected chromosomal target region within that genome. An example of nonspecific binding DNA comprises a class of DNA repeated segments whose members commonly occur in more than one chromosome or chromosome region. Such common repetitive segments tend to hybridize to a greater extent than other DNA segments that are present in probe composition.

As used herein, the term "stratification" refers to the creation of a distinction between subjects on the basis of a characteristic or characteristics of the subjects. Generally, in the context of clinical trials, the distinction is used to distinguish responses or effects in different sets of patients distinguished according to the stratification parameters. In some embodiments, stratification includes distinction of subject groups based on the presence or absence of an OPRP genetic signature described herein. The stratification can be performed, e.g., in the course of analysis, or can be used in creation of distinct groups or in other ways.

As used herein, "Typical" antipsychotics refer to so called first generation or classical antipsychotics. This class of drugs was first developed in the 1950s. Some examples include: Chlorpromazine (Largactil, Thorazine), Fluphenazine (Prolixin), Haloperidol (Haldol, Serenace), Molindone, Thiothixene (Navane), Thioridazine (Mellaril), Trifluoperazine (Stelazine), Loxapine (Loxapac, Loxitane), Perphenazine, Prochlorperazine (Compazine, Buccastem, Stemetil), Pimozide (Orap), Zuclopenthixol (Clopixol). This class of drug can cause serious adverse events, particularly Tardive Dyskinesia, a movement disorder.

As used herein, "Atypical" antipsychotics refer to a newer class of antipsychotic drugs first introduced in the 1990s. This class of drugs includes the following examples:

Clozapine (Clozaril) (FDA-approval: 1990) Available in oral tablets and dissolving tablets (FazaClo).

Risperidone (Risperdal) (FDA-approval: 1993) Available in oral tablets, dissolving tablets, liquid form, and extended release intramusclar injection.

Olanzapine (Zyprexa) (FDA-approval: 1996) Available in oral tablets, dissolving tablets, and intramuscular injection.

Quetiapine (Seroquel) (FDA-approval: 1997) Available only in oral tablets.

Ziprasidone (Geodon) (FDA-approval: 2001) Available in oral capsules and intramuscular injection.

Aripiprazole (Abilify) (FDA)-approval: 2002) Available in oral tablets and dissolving tablets.

Paliperidone (Invega) (FDA)-approval: 2006) Available in extended-release oral tablets.

Asenapine FDA has accepted NDA as of Nov. 26, 2007.

Iloperidone (Fanapta or Zomaril) FDA has accepted NDA as of Nov. 27, 2007.

Sertindole (Serlect) (Not approved by the FDA for use in the USA).

Zotepine (Not approved by the FDA for use in the USA).

Amisulpride (Not approved by the FDA for use in the USA).

Bifeprunox (Not approved by the FDA for use in the USA).

Melperone Approved in Europe. Currently in clinical trial in the USA

Atypicals have a superior side-effect profile for the serious adverse event Tardive Dyskinesia. However, the atypicals can cause metabolic disturbances leading to weight gain and metabolic syndrome.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

II. OPRP Genetic Signature

In certain aspects, the present invention involves determination of an OPRP genetic signature and use of the specific genetic signature to optimize treatments for psychotic disorders. For example, the invention may enhance drug safety and improve treatment outcome.

The synaptic vesicle glycoprotein 2C gene (SV2C) is located on chromosome 5q (from 75,379,305 to 75,621,416 by Consortium Human Build 37 (GRCh37), Primary_Assembly; source: available on the world wide web at www.ncbi.nlm.nih.gov/gene/22987). It encodes the SV2C protein, which is expressed in the brain and interacts with synaptotagmin 1 to regulate neurotransmitter release in a variety of synapses (Lazzell et al., 2004: Schivell et al., 2005; Xu et al., 2001; Janz et al., 1999). Determination of the genotype of SNP marker rs11960832, which is located within the SV2C gene, comprises one aspect of the OPRP genetic signature test.

The mannosyl (alpha-1,3-)-glycoprotein beta-1,4-N-acetylglucosaminyltransferase, isozyme C (putative) gene (MGAT4C) is located on chromosome 12 q (from 86,373,037 to 87,232,681 by Consortium Human Build 37 (GRCh37), Primary_Assembly; source: available on the world wide web at www.ncbi.nlm.nih.gov/gene/25834). It encodes the MGAT4C protein and is expressed in the fetal and adult brain (Furukawa et al., 1999). Determination of the genotype of SNP marker rs7975477, which is located within the MGAT4C gene, comprises one aspect of the OPRP genetic signature test.

The OPRP genetic signature was selected as the biomarker of interest based on results showing associations between this genetic signature and response to antipsychotic drugs. The inventors used samples from the Clinical Antipsychotic Trials of Intervention Effectiveness (CATIE), a large federally funded clinical trial designed to assess the efficacy of antipsychotics in a real world setting (Lieberman et al., 2005; Stroup et al., 2003), to explore gene-based differential responses of patients suffering from schizophrenia and related disorders (schizoaffective disorder and bipolar disorder) to atypical antipsychotic drugs.

The OPRP genetic signature occurs at a frequency of approximately 6.5% in Caucasians and 23.5% in African Americans.

III. Determination of OPRP Genetic Signature

The invention includes methods for determination of the OPRP genetic signature in order to select optimal treatments. Homozygosity for a SNP within the SV2C gene, i.e., SNP rs11960832(T)/rs11960832(T) homozygosity, in combination with either a homozygous or heterozygous T allele at marker rs7975477 within the MGAT4C gene, i.e., rs7975477 (T)/rs7975477(T) homozygosity or rs7975477(T)/rs7975477 (C) heterozygosity, can be used to determine a OPRP genetic signature as defined above. Using the exemplary SNP markers (i.e., rs11960832 and rs7975477) or SNPS in linkage disequilibrium with the exemplary SNPs, one can determine the presence or absence of an OPRP genetic signature. Using the genetic signature, one can assign subjects to specific categories based on the evaluation of the genetic signature present in the subject and select optimal treatments (atypical antipsychotic, typical antipsychotic, and/or psychosocial intervention) for patients.

Determining an OPRP genetic signature can, but need not, include obtaining a sample comprising DNA from a subject, and/or assessing the identity, presence or absence of one or more genetic markers for the OPRP genetic signature in the sample. The individual or organization who determines the genetic signature need not actually carry out the physical analysis of a sample from a subject; the genetic signature can include information obtained by analysis of the sample by a third party. Thus the methods can include steps that occur at more than one site. For example, a sample can be obtained from a subject at a first site, such as at a health care provider or at the subject's home in the case of a self-testing kit. The sample can be analyzed at the same or a second site, e.g., at a laboratory, a sequencing or genotyping facility, or other testing facility. Determining a genetic signature can also include or consist of reviewing a subject's medical history or test results, where the medical history or test results includes information regarding the identity, presence or absence of one or more genetic markers in the subject.

Samples that are suitable for use in the methods described herein contain genetic material, e.g., genomic DNA (gDNA). Non-limiting examples of sources of samples include urine, blood, cells, and tissues. The sample itself will typically consist of nucleated cells (e.g., blood or buccal cells), tissue, etc., removed from the subject. The subject can be an adult, a child, a fetus, or an embryo. In some embodiments, the sample is obtained prenatally, either from a fetus or an embryo or from the mother (e.g., from fetal or embryonic cells in the maternal circulation). Methods and reagents are known in the art for obtaining, processing, and/or analyzing samples. In some embodiments, the sample is obtained with the assistance of a health care provider, e.g., to draw blood. In some embodiments, the sample is obtained without the assistance of a health care provider, e.g., where the sample is obtained non-invasively, such as a sample comprising buccal cells that is obtained using a buccal swab or brush, or a mouthwash sample.

The sample may be further processed before the detecting step. For example, DNA in a cell or tissue sample can be separated from other components of the sample. The sample can be concentrated and/or purified to isolate DNA. Cells can be harvested from a biological sample using standard techniques known in the art. For example, cells can be harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract DNA, e.g., gDNA. See, e.g., Ausubel et al., 2003, supra. All samples obtained from a subject, including those subjected to any sort of further processing, are considered to be obtained from the subject.

OPRP genetic signature may be determined by any methods known in the art, e.g., gel electrophoresis, capillary electrophoresis, size exclusion chromatography, sequencing, and/or arrays to detect the presence or absence of the marker(s) of the genetic signature. Amplification of nucleic acids, where desirable, can be accomplished using methods known in the art, e.g., PCR.

Methods of nucleic acid analysis to detect polymorphisms and/or polymorphic variants include, e.g., microarray analysis. Hybridization methods, such as Southern analysis, Northern analysis, or in situ hybridizations, can also be used (see Ausubel et al., 2003). To detect microdeletions, fluorescence in situ hybridization (FISH) using DNA probes that are directed to a putatively deleted region in a chromosome can be used. For example, probes that detect all or a part of a microsatellite marker can be used to detect microdeletions in the region that contains that marker.

Other methods include direct manual sequencing (Church and Gilbert, 1988; Sanger et al., 1977; U.S. Pat. No. 5,288, 644); automated fluorescent sequencing; single-stranded conformation polymorphism assays (SSCP); clamped denaturing gel electrophoresis (CDGE); two-dimensional gel electrophoresis (2DGE or TDGE); conformational sensitive gel electrophoresis (CSGE); denaturing gradient gel electrophoresis (DGGE) (Sheffield et al., 1989), mobility shift analysis (Orita et al., 1989), restriction enzyme analysis (Flavell et al., 1978; Geever et al., 1981); quantitative real-time PCR (Raca et al., 2004); heteroduplex analysis; chemical mismatch cleavage (CMC) (Cotton et al., 1985); RNase protection assays (Myers et al., 1985); use of polypeptides that recognize nucleotide mismatches, e.g., *E. coli* mutS protein; allele-specific PCR, for example. See, e.g., U.S. Patent Publication No. 2004/0014095, to Gerber et al., which is incorporated herein by reference in its entirety. In some embodiments, the sequence is determined on both strands of DNA.

In order to detect polymorphisms and/or polymorphic variants, it will frequently be desirable to amplify a portion of genomic DNA (gDNA) encompassing the polymorphic site. Such regions can be amplified and isolated by PCR using oligonucleotide primers designed based on genomic and/or cDNA sequences that flank the site. See e.g., *PCR Primer: A Laboratory Manual*; McPherson et al., 2000; Mattila et al., 1991; Eckert et al., 1991; and U.S. Pat. No. 4,683,202. Other amplification methods that may be employed include the ligase chain reaction (LCR) (Wu and Wallace, 1989, Landegren et al., 1988), transcription amplification (Kwoh et al., 1989), self-sustained sequence replication (Guatelli et al., 1990), and nucleic acid based sequence amplification (NASBA). Guidelines for selecting primers for PCR amplification are well known in the art. See, e.g., McPherson et al. (2000). A variety of computer programs for designing primers are available, e.g., 'Oligo' (National Biosciences, Inc, Plymouth Minn.), MacVector (Kodak/IBI), and the GCG suite of sequence analysis programs (Genetics Computer Group, Madison, Wis. 53711).

In one example, a sample (e.g., a sample comprising genomic DNA), is obtained from a subject. The DNA in the sample is then examined to determine a OPRP genetic signature as described herein. The genetic signature can be determined by any method described herein, e.g., by sequencing or by hybridization of the gene in the genomic DNA, RNA, or cDNA to a nucleic acid probe, e.g., a DNA probe (which includes cDNA and oligonucleotide probes) or an RNA probe. The nucleic acid probe can be designed to specifically or preferentially hybridize with a particular polymorphic variant.

In some embodiments, a peptide nucleic acid (PNA) probe can be used instead of a nucleic acid probe in the hybridization methods described above. PNA is a DNA mimetic with a peptide-like, inorganic backbone, e.g., N-(2-aminoethyl)glycine units, with an organic base (A, G, C, T or U) attached to the glycine nitrogen via a methylene carbonyl linker (see, e.g., Nielsen et al., 1994). The PNA probe can be designed to specifically hybridize to a nucleic acid comprising a polymorphic variant of the OPRP genetic signature.

In some embodiments, restriction digest analysis can be used to detect the existence of a polymorphic variant of a polymorphism, if alternate polymorphic variants of the polymorphism result in the creation or elimination of a restriction site. A sample containing genomic DNA is obtained from the individual. Polymerase chain reaction (PCR) can be used to amplify a region comprising the polymorphic site, and restriction fragment length polymorphism analysis is conducted (see Ausubel et al., supra). The digestion pattern of the relevant DNA fragment may indicate the presence or absence of a particular polymorphic variant of the OPRP genetic signature and may be therefore indicative of the presence or absence of the OPRP genetic signature.

Sequence analysis can also be used to detect specific polymorphic variants. A sample comprising DNA or RNA is obtained from the subject. PCR or other appropriate methods can be used to amplify a portion encompassing the polymorphic site, if desired. The sequence is then ascertained, using any standard method, and the presence of a polymorphic variant is determined.

Allele-specific oligonucleotides can also be used to detect the presence of a polymorphic variant, e.g., through the use of dot-blot hybridization of amplified oligonucleotides with allele-specific oligonucleotide (ASO) probes (see, for example, Saiki et al., 1986). An "allele-specific oligonucleotide" (also referred to herein as an "allele-specific oligonucleotide probe") is typically an oligonucleotide of approximately 10-50 base pairs, preferably approximately 15-30 base pairs, that specifically hybridizes to a nucleic acid region that contains a polymorphism. An allele-specific oligonucleotide probe that is specific for a particular polymorphism can be prepared using standard methods (see Ausubel et al., supra).

Generally, to determine which of multiple polymorphic variants is present in a subject, a sample comprising DNA is obtained from the individual. PCR can be used to amplify a portion encompassing the polymorphic site. DNA containing the amplified portion may be dot-blotted, using standard methods (see Ausubel et al., supra), and the blot contacted with the oligonucleotide probe. The presence of specific hybridization of the probe to the DNA is then detected. Specific hybridization of an allele-specific oligonucleotide probe (specific for a polymorphic variant indicative of susceptibility to altered pharmacological response) to DNA from the subject may determine a OPRP genetic signature.

In some embodiments, fluorescence polarization template-directed dye-terminator incorporation (FP-TDI) is used to determine which of multiple polymorphic variants of a polymorphism is present in a subject (Chen et al., 1999). Rather than involving use of allele-specific probes or primers, this method employs primers that terminate adjacent to a polymorphic site, so that extension of the primer by a single nucleotide results in incorporation of a nucleotide complementary to the polymorphic variant at the polymorphic site.

Real-time pyrophosphate DNA sequencing is yet another approach to detection of polymorphisms and polymorphic variants (Alderborn et al., 2000). Additional methods include, for example, PCR amplification in combination with denaturing high performance liquid chromatography (dHPLC) (Underhill et al., 1997).

The methods can include determining the genotype of a subject with respect to both copies of the polymorphic site present in the genome. For example, the complete genotype may be characterized as −/−, as −/+, or as +/+, where a plus sign indicates the presence of the polymorphic variant of interest, such as rs11960832(T) or rs7975477(T), and a minus sign indicates the absence of the polymorphic variant of interest and/or the presence of the other or wild type sequence at the polymorphic site. If multiple polymorphic variants exist at a site, this can be appropriately indicated by specifying which ones are present in the subject. Any of the detection means described herein can be used to determine the genotype of a subject with respect to one or both copies of the polymorphism present in the subject's genome.

In some embodiments, it is desirable to employ methods that can detect the presence of multiple polymorphisms (e.g., polymorphic variants at a plurality of polymorphic sites) in parallel or substantially simultaneously. Oligonucleotide arrays represent one suitable means for doing so. Other methods, including methods in which reactions (e.g., amplification, hybridization) are performed in individual vessels, e.g., within individual wells of a multi-well plate or other vessel may also be performed so as to detect the presence of multiple polymorphic variants (e.g., polymorphic variants at a plurality of polymorphic sites) in parallel or substantially simultaneously according to certain embodiments of the invention.

IV. Psychotic Disorders

Certain aspects of the invention can use OPRP genetic signature status to optimize treatments for psychotic disorders, such as schizophrenia (SZ), schizotypal personality disorder (SPD), schizoaffective disorder (SD), and/or bipolar disorders (BD).

Schizophrenia and bipolar disorder are life-long, severely disabling mental illnesses. The clinical criteria for these neuropsychiatric illnesses have continued to evolve through a consensus process organized by the American Psychiatric Association (APA) and published in its Diagnostic and Statistical Manual (DSM) I-IV (American Psychiatric Assoc. Diagnostic and Statistical Manual of Mental Disorders, 1994). The inventors disclose here some of the key features of both illnesses as currently conceived, with the full awareness that there is strong evidence for overlap between these disorders in genetic risk factors and response to treatment. Nevertheless, all indications are that DSM-V, which is currently being developed by the APA, will maintain this distinction more or less in the current form. Also because FDA indications for treatment have been and may continue to be given for drugs for each disorder separately, having genetic information which pertains to classification and prediction of response to treatment is of considerable value.

Schizophrenia and bipolar disorder share some common clinical features while differing on others. Schizophrenia is characterized by psychotic symptoms (delusions, hallucinations), disorganized thinking and cognitive impairment and poor social and work function. Additionally, some schizophrenia patients can have severe negative symptoms, including blunted affect and social and emotional withdrawal. Bipolar Disorder is characterized by two main types of mood disturbances, with depression being the most common type and mania, or hypomania less frequent. Psychotic disorders may be present in either the manic or depressive mood phases. Both disorders have a high risk for suicide attempts and completions.

Schizophrenia usually begins in the late teens and early 20's. It affects about 1% of the population. Conversely, bipolar disorder most often occurs in the $3^{rd}$ and $4^{th}$ decades of life. Bipolar (BP) Type I affects about 1.5% of the population. BP type II and BP Not Otherwise Specified (NOS) afflict another 2-4% of the population. Life-long drug treatment is often required to minimize the number of acute episodes, the need for hospitalization or assisted living, and to optimize daily functioning. Suicide occurs in 5% of schizophrenia cases and 10% of bipolar disorder cases. Patients with schizophrenia or bipolar disorder can have "acute" episodes which are characterized by abrupt and large increases in psychotic symptoms. Often, these episodes occur after a period of non-compliance with medication. Both are generally treated with one or more classes of psychotropic medications. Atypical antipsychotic drugs treat psychosis and mood disturbances. Additionally, mood stabilizers such as lithium or valproate treat the manic phase of bipolar disorder, and antidepressants and atypical antipsychotic drugs target the depressive phase. Antipsychotics and mood stabilizers are often used together for "maintenance" treatment to prevent relapse.

A. Schizophrenia (SZ)

SZ is considered a clinical syndrome, and is probably a constellation of several pathologies. Substantial heterogeneity is seen between cases; this is thought to reflect multiple overlapping etiologic factors, including both genetic and environmental contributions. A diagnosis of SZ is typically indicated by chronic psychotic symptoms, e.g., hallucinations and delusions. Disorganization of thought and behavior are common and are considered distinguishing factors in the diagnosis of SZ. Patients typically have some subtle impairments in cognition. Reduced emotional experience and expression, low drive, and impaired speech are observed in a subgroup of patients. Cognitive, emotional and social impairments often appear early in life, while the psychotic symptoms typically manifest in late adolescence or early adulthood in men, a little later in women.

A diagnosis of SZ can be made according to the criteria reported in the *Diagnostic and Statistical Manual of Mental Disorders, Fourth Edition, Text Revision*, American Psychiatric Association, 2000 (referred to herein as DSM-IV) as follows:

Diagnostic Criteria for SZ—All six criteria must be met for a diagnosis of SZ.

A. Characteristic symptoms: Two (or more) of the following, each present for a significant portion of time during a one month period (or less if successfully treated):

(1) delusions; (2) hallucinations; (3) disorganized speech (e.g., frequent derailment or incoherence); (4) grossly disorganized or catatonic behavior; (5) negative symptoms, e.g., affective flattening, alogia, or avolition.

Only one criterion A symptom is required if delusions are bizarre or hallucinations consist of a voice keeping up a running commentary on the person's behavior or thoughts, or two or more voices conversing with each other.

B. Social/occupational dysfunction: For a significant portion of the time since the onset of the disturbance, one or more major areas of functioning such as work, interpersonal relations, or self-care are markedly below the level achieved prior to the onset (or when the onset is in childhood or adolescence, failure to achieve expected level of interpersonal, academic, or occupational achievement).

C. Duration: Continuous signs of the disturbance persist for at least 6 months. This 6-month period must include at least 1 month of symptoms (or less if successfully treated) that meet Criterion A (i.e., active-phase symptoms) and may include periods of prodromal or residual symptoms. During these prodromal or residual periods, the signs of the disturbance may be manifested by only negative symptoms or two or more symptoms listed in Criterion A present in an attenuated form (e.g., odd beliefs, unusual perceptual experiences).

D. Schizoaffective and Mood Disorder Exclusion: Schizoaffective Disorder and Mood Disorder With Psychotic Features have been ruled out because either (1) no major depressive, manic, or mixed episodes have occurred concurrently with the active-phase symptoms; or (2) if mood episodes have occurred during active-phase symptoms, their total duration has been brief relative to the duration of the active and residual periods.

E. Substance/General Medical Condition Exclusion: The disturbance is not due to the direct physiological effects of a substance (e.g., a drug of abuse, a medication) or a general medical condition.

F. Relationship to a Pervasive Developmental Disorder: If the patient has a history of Autistic Disorder or another Pervasive Developmental Disorder, the additional diagnosis of SZ is made only if prominent delusions or hallucinations are also present for at least a month (or less if successfully treated).

B. Schizoaffective Disorder (SD)

SD is characterized by the presence of affective (depressive or manic) symptoms and schizophrenic symptoms within the same, uninterrupted episode of illness.

The DSM-IV Criteria for a diagnosis of schizoaffective disorder is as follows:

An uninterrupted period of illness during which, at some time, there is either (1) a Major Depressive Episode (which must include depressed mood), (2) a Manic Episode, or (3) a Mixed Episode, concurrent with symptoms that meet (4) Criterion A for SZ, above.

A. Criteria for Major Depressive Episode

At least five of the following symptoms must be present during the same 2-week period and represent a change from previous functioning; at least one of the symptoms is either (1) depressed mood or (2) loss of interest or pleasure.

(1) depressed mood most of the day, nearly every day, as indicated by either subjective report (e.g., feels sad or empty) or observation made by others (e.g., appears tearful). In children and adolescents, this can be an irritable mood.

(2) markedly diminished interest or pleasure in all, or almost all, activities most of the day, nearly every day (as indicated by either subjective account or observation made by others)

(3) significant weight loss when not dieting or weight gain (e.g., a change of more than 5% of body weight in a month), or decrease or increase in appetite nearly every day. (In children, failure to make expected weight gains is considered).

(4) insomnia or hypersomnia nearly every day (5) psychomotor agitation or retardation nearly every day (observable by others, not merely subjective feelings of restlessness or being slowed down)

(6) fatigue or loss of energy nearly every day (7) feelings of worthlessness or excessive or inappropriate guilt (which may be delusional) nearly every day (not merely self-reproach or guilt about being sick)

(8) diminished ability to think or concentrate, or indecisiveness, nearly every day (either by subjective account or as observed by others)

(9) recurrent thoughts of death (not just fear of dying), recurrent suicidal ideation without a specific plan, or a suicide attempt or a specific plan for committing suicide In addition, the symptoms do not meet criteria for a Mixed Episode. The symptoms cause clinically significant distress or impairment in social, occupational, or other important areas of functioning. The symptoms are not due to the direct physiological effects of a substance (e.g., a drug of abuse, a medication) or a general medical condition (e.g., hypothyroidism).

The symptoms are not better accounted for by Bereavement, i.e., after the loss of a loved one, the symptoms persist for longer than 2 months, or are characterized by marked functional impairment, morbid preoccupation with worthlessness, suicidal ideation, psychotic symptoms, or psychomotor retardation.

B. Criteria for Manic Episode

A manic episode is a distinct period of abnormally and persistently elevated, expansive, or irritable mood, lasting at least one week (or any duration, if hospitalization is necessary).

During the period of mood disturbance, three (or more) of the following symptoms have persisted (four if the mood is only irritable) and have been present to a significant degree:

(1) inflated self-esteem or grandiosity (2) decreased need for sleep (e.g., feels rested after only 3 hours of sleep)

(3) more talkative than usual or pressure to keep talking (4) flight of ideas or subjective experience that thoughts are racing (5) distractibility (i.e., attention too easily drawn to unimportant or irrelevant external stimuli)

(6) increase in goal-directed activity (either socially, at work or school, or sexually) or psychomotor agitation (7) excessive involvement in pleasurable activities that have a high potential for painful consequences (e.g., engaging in unrestrained buying sprees, sexual indiscretions, or foolish business investments)

The symptoms do not meet criteria for a Mixed Episode. The mood disturbance is sufficiently severe to cause marked impairment in occupational functioning or in usual social activities or relationships with others, or to necessitate hospitalization to prevent harm to self or others, or there are psychotic features. The symptoms are not due to the direct physiological effects of a substance (e.g., a drug of abuse, a medication, or other treatment) or a general medical condition (e.g., hyperthyroidism).

C. Criteria for Mixed Episode

A mixed episode occurs when the criteria are met both for a Manic Episode and for a Major Depressive Episode (except for duration) nearly every day during at least a 1-week period. The mood disturbance is sufficiently severe to cause marked impairment in occupational functioning or in usual social activities or relationships with others, or to necessitate hospitalization to prevent harm to self or others, or there are psychotic features.

The symptoms are not due to the direct physiological effects of a substance (e.g., a drug of abuse, a medication, or other treatment) or a general medical condition (e.g., hyperthyroidism).

D. Criterion A of SZ

See above.

E. Types of SD

The type of SD may be may be specifiable, as either Bipolar Type, if the disturbance includes a Manic or a Mixed Episode (or a Manic or a Mixed Episode and Major Depressive Episodes), or Depressive Type, if the disturbance only includes Major Depressive Episodes.

F. Associated Features

Features associated with SD include Learning Problems, Hypoactivity, Psychotic, Euphoric Mood, Depressed Mood, Somatic/Sexual Dysfunction, Hyperactivity, Guilt/Obsession, Odd/Eccentric/Suspicious Personality, Anxious/Fearful/Dependent Personality, and Dramatic/Erratic/Antisocial Personality.

C. Schizotypal Personality Disorder (SPD)

A diagnosis of SPD under the criteria of the DSM-IV is generally based on a pervasive pattern of social and interpersonal deficits marked by acute discomfort with, and reduced capacity for, close relationships as well as by cognitive or perceptual distortions and eccentricities of behavior, beginning by early adulthood and present in a variety of contexts, as indicated by five (or more) of the following:

(1) ideas of reference (excluding delusions of reference)

(2) odd beliefs or magical thinking that influences behavior (3) inconsistent with subcultural norms (e.g., superstitiousness, belief in clairvoyance, telepathy, or "sixth sense;" in children and adolescents, bizarre fantasies or preoccupations)

(4) unusual perceptual experiences, including bodily illusions (5) odd thinking and speech (e.g., vague, circumstantial, metaphorical, overelaborate, or stereotyped)

(6) suspiciousness or paranoid ideation (7) inappropriate or constricted affect (8) behavior or appearance that is odd, eccentric, or peculiar (9) lack of close friends or confidants other than first-degree relatives

(10) excessive social anxiety that does not diminish with familiarity and tends to be associated with paranoid fears rather than negative judgments about self SPD is diagnosed if the symptoms do not occur exclusively during the course of SZ, a Mood Disorder With Psychotic Features, another Psychotic Disorder, or a Pervasive Developmental Disorder, and the disturbance is not due to the direct physiological effects of a substance (e.g., a drug of abuse, a medication) or a general medical condition.

Associated features of SPD include Depressed Mood and Odd/Eccentric/Suspicious Personality.

D. Bipolar Disorder (BD)

Bipolar disorder is also known as manic-depression or manic-depressive disorder. This condition is characterized by mood that alternates between two emotional extremes, or poles: the sadness of depression and the euphoria of mania (see symptoms of mania below).

Between these emotional swings, there are periods when a person's mood is quite normal. When a person is in the depressed phase of bipolar illness, he or she will have the same symptoms as those found in major depressive disorder. The depressive episodes can often be severe. While in a manic phase, a person experiences mood that is extremely elevated, expansive, or irritable. Mania can seriously impair one's normal judgment. When manic, a person is prone towards reckless and inappropriate behavior such as engaging in wild spending sprees or having promiscuous sex. He or she may not be able to realize the harm of his/her behavior and may even lose touch with reality.

There are two primary types of bipolar disorder:

Bipolar I Disorder is diagnosed when a person has had at least one manic or mixed episode, often along with a major depressive episode. It affects equal numbers of men and women in approximately 0.4% to 1.6% of the population.

Bipolar II Disorder is diagnosed when a person has had a major depressive episode along with at least one hypomanic episode. It affects more women than men in about 0.5% of the population.

People with bipolar disorder experience a wide range of feelings depending on the phase of the illness is present. During a phase of depression, a person will have many of the symptoms of a major depressive episode. He or she may have despondent mood, a loss of energy, feelings of worthlessness or guilt, or problems with concentration. Thoughts of suicide are not uncommon. In fact, 10% to 15% of those with bipolar disorder may die by suicide. If the depression is severe, a person may need to be hospitalized for his or her own safety. For those who go through a phase of hypomania, the experience usually feels quite good. If a person's mood and spirit lightens, he or she will be more outgoing and notice more energy and enhanced self-esteem. Lots of ideas come with ease and a person may feel compelled towards greater activity and productivity. A person in a hypomanic phase may also feel more powerful and omnipotent.

The manic phase is the most extreme part of bipolar disorder. A person becomes euphoric, ideas come much too fast, and concentration is nearly impossible. Anger, irritability, fear, and a sense of being out of control are overwhelming. A person's judgment is impaired, and he or she may behave recklessly without a sense of consequence. Some people lose touch with reality and experience delusions and hallucinations. When this happens, people often need to be hospitalized for their own safety. If a person with bipolar disorder experiences a severe manic episode, he or she may be abusive to children, spouses, or engage in other violent behaviors. There may also be problems with attendance and performance at school or work, as well as significant difficulties in personal relationships.

The cycles of bipolar disorder may be different for each person. Oftentimes a person may first experience depression. Then depression may be replaced with manic symptoms and the cycle between depression and mania may continue for days, weeks, or months. Between phases of depression and mania some people return to their normal mood. Some others have several periods of either depression or mania. Still others may experience several bouts of depression with infrequent phases of hypomania, or repeated manic episodes with occasional depressive periods. A portion of people, roughly 10% to 20% may only experience mania, while others can have both depression and mania at the same time.

For at least 90% of those who have bipolar disorder the condition is recurrent. They will experience future symptoms of the cycles of mania and depression. Approximately 60%-70% of manic episodes may happen just before or after a depressive episode, and this pattern may happen in a particular way for each person. Most people return to a regular level of functioning between episodes, while some (about 20%-30%) may continue to have some problems with mood stability and social and occupational functioning.

Bipolar I disorder affects equal numbers of males and females, however there does appear to be a gender difference in the onset of the illness. Females are more likely to experience a first episode of depression, while males tend to have a first episode that is manic. Women who have bipolar I or II disorder and who have children may be at a higher risk of experiencing bipolar episodes within several months of giving birth.

A first episode of mania is most likely to occur when a person is in his/her teens or twenties. If a person develops bipolar disorder for the first time after 40 years of age, he or she should be evaluated for the possibility of a medical illness or substance use.

People who have immediate relatives with bipolar I disorder have a higher risk of developing a mood disorder themselves. For these people the rate of developing bipolar II disorder or major depression is 4%-24% and bipolar I disorder is 1%-5%.

Of adolescents who have recurrent major depressive episodes, about 10%-15% of them will likely develop bipolar disorder.

Diagnostic Criteria of Bipolar I Disorder

Summarized from the Diagnostic and *Statistical Manual of Mental Disorders—Fourth Edition*

A. A person experiences a current or recent episode that is manic, hypomanic, mixed, or depressed.

To be a manic episode, for at least one week a person's mood must be out of the ordinary and continuously heightened, exaggerated, or irritable.

At least three of the following seven symptoms have been significant and enduring. If the mood is only irritable, then four symptoms are required.

Self-esteem is excessive or grandiose.

The need for sleep is greatly reduced.

Talks much more than usual.

Thoughts and ideas are continuous and without a pattern or focus.

Easily distracted by unimportant things.

An increase in purposeful activity or productivity, or behaving and feeling agitated.

Reckless participation in enjoyable activities that create a high risk for negative consequences (e.g., extensive spending sprees, sexual promiscuity).

The persons' symptoms do not indicate a mixed episode.

The person's symptoms are a cause of great distress or difficulty in functioning at home, work, or other important areas. Or, the symptoms require the person to be hospitalized to protect the person from harming himself/herself or others. Or, the symptoms include psychotic features (hallucinations, delusions).

The person's symptoms are not caused by substance use (e.g., alcohol, drugs, medication), or a medical disorder.

B. Unless this is a first single manic episode there has been at least one manic, mixed, hypomanic, or depressive episode.

For a major depressive episode a person must have experienced at least five of the nine symptoms below for the same two weeks or more, for most of the time almost every day, and this is a change from his/her prior level of functioning. One of the symptoms must be either (a) depressed mood, or (b) loss of interest.

Depressed mood. For children and adolescents, this may be irritable mood.

A significantly reduced level of interest or pleasure in most or all activities.

A considerable loss or gain of weight (e.g., 5% or more change of weight in a month when not dieting). This may also be an increase or decrease in appetite. For children, they may not gain an expected amount of weight.

Difficulty falling or staying asleep (insomnia), or sleeping more than usual (hypersomnia).

Behavior that is agitated or slowed down. Others should be able to observe this.

Feeling fatigued, or diminished energy.

Thoughts of worthlessness or extreme guilt (not about being ill).

Ability to think, concentrate, or make decisions is reduced.

Frequent thoughts of death or suicide (with or without a specific plan), or attempt of suicide.

The persons' symptoms do not indicate a mixed episode.

The person's symptoms are a cause of great distress or difficulty in functioning at home, work, or other important areas.

The person's symptoms are not caused by substance use (e.g., alcohol, drugs, medication), or a medical disorder.

The person's symptoms are not due to normal grief or bereavement over the death of a loved one, they continue for more than two months, or they include great difficulty in functioning, frequent thoughts of worthlessness, thoughts of suicide, symptoms that are psychotic, or behavior that is slowed down (psychomotor retardation).

C. Another disorder does not better explain the episode.

Diagnostic Criteria of Bipolar II Disorder

Summarized from the *Diagnostic and Statistical Manual of Mental Disorders—Fourth Edition*

A. The person currently has, or in the past has had at least one major depressive episode:

For a major depressive episode a person must have experienced at least five of the nine symptoms below for the same two weeks or more, for most of the time almost every day, and this is a change from his/her prior level of functioning. One of the symptoms must be either (a) depressed mood, or (b) loss of interest.

Depressed mood. For children and adolescents, this may be irritable mood.

A significantly reduced level of interest or pleasure in most or all activities.

A considerable loss or gain of weight (e.g., 5% or more change of weight in a month when not dieting). This may also be an increase or decrease in appetite. For children, they may not gain an expected amount of weight.

Difficulty falling or staying asleep (insomnia), or sleeping more than usual (hypersomnia).

Behavior that is agitated or slowed down. Others should be able to observe this.

Feeling fatigued, or diminished energy.

Thoughts of worthlessness or extreme guilt (not about being ill).

Ability to think, concentrate, or make decisions is reduced.

Frequent thoughts of death or suicide (with or without a specific plan), or attempt of suicide.

The persons' symptoms do not indicate a mixed episode.

The person's symptoms are a cause of great distress or difficulty in functioning at home, work, or other important areas.

The person's symptoms are not caused by substance use (e.g., alcohol, drugs, medication), or a medical disorder.

The person's symptoms are not due to normal grief or bereavement over the death of a loved one, they continue for more than two months, or they include great difficulty in functioning, frequent thoughts of worthlessness, thoughts of suicide, symptoms that are psychotic, or behavior that is slowed down (psychomotor retardation).

B. The person currently has, or in the past has had at least one hypomanic episode:

For a hypomanic episode a person's mood must be out of the ordinary and continuously heightened, exaggerated, or irritable for at least four days.

At least three of the following seven symptoms have been significant and enduring. If the mood is only irritable, then four symptoms are required.

Self-esteem is excessive or grandiose.

The need for sleep is greatly reduced.

Talks much more than usual.

Thoughts and ideas are continuous and without a pattern or focus.

Easily distracted by unimportant things.

An increase in purposeful activity or productivity, or behaving and feeling agitated.

Reckless participation in enjoyable activities that create a high risk for negative consequences (e.g., extensive spending sprees, sexual promiscuity).

The episode is a substantial change for the person and uncharacteristic of his or her usual functioning.

The changes of functioning and mood can be observed by others.

The person's symptoms are NOT severe enough to cause difficulty in functioning at home, work, or other important areas. Also, the symptoms neither require the person to be hospitalized, nor are there any psychotic features.

The person's symptoms are not caused by substance use (e.g., alcohol, drugs, medication), or a medical disorder. C. The person has never experienced a manic or mixed episode. D. Another disorder does not better explain the episode. E. The symptoms are a cause of great distress or difficulty in functioning at home, work, or other important areas.

E. Psychiatric Endophenotypes in SZ

A number of endophenotypes, i.e., intermediate phenotypes, that may more closely reflect biological mechanisms behind SZ, have been suggested, such as prepulse inhibition, structural abnormalities evident in MRI scans, specific domains of cognition (e.g., executive function), fine motor performance, working memory, etc.

Endophenotypes can also include clinical manifestations such as hallucinations, paranoia, mania, depression, obsessive-compulsive symptoms, etc., as well as response or lack of response to drugs and comorbidity for substance and alcohol abuse. See, e.g., Kendler et al. (1995); Gottesman and Gould (2003); Cadenhead, 2002; Heinrichs (2004); and Zobel and Maier (2004). There is now evidence that some candidate genes that were identified using DSM-IV type categorical definitions for "affected" individuals may influence specific endophenotypes, see, e.g., Baker et al. (2005); Cannon et al. (2005); Gothelf et al. (2005); Hallmayer et al. (2005); Callicott et al. (2005); Gornick et al. (2005).

F. Use of PANSS (Positive and Negative Syndrome Scale) Score for Differential Diagnosis and Evaluation of Clinical Response The Positive and Negative Syndrome Scale (PANSS) is a comprehensive psychometric scale used to classify psychopathology for severe neuropsychiatric diseases, including SZ. It measures a number of psychiatric endophenotypes or dimensions using quantitative scales based on the scoring of patients by clinicians. It is widely used to classify patients into specific subtypes, and is commonly used for measuring the improvement of symptoms in response to clinical interventions (Kay et al., 1987; Kay et al., 1989; Leucht et al., 2005).

Detailed information on PANSS and Scoring Criteria can be found in the art, e.g., on the world wide web at panss.org, or in the book by Kay (1991) which is incorporated herein in its entirety by reference. Based on these sources, the methodology is summarized briefly below.

PANSS comprises 30 individual subscales. Seven constitute a Positive Symptom Scale, seven the Negative Symptom Scale, and the remaining 16 items make up a General Psychopathology Scale. The scores for these scales are arrived at by summation of ratings across component items. Therefore, the potential ranges are 7 to 49 for the Positive and Negative Scales, and 16 to 112 for the General Psychopathology Scale (Source: The PANSS Institute).

Each of the 30 items is accompanied by a specific definition as well as detailed anchoring criteria for all seven rating points. These seven points represent increasing levels of psychopathology, as follows:
1—absent
2—minimal
3—mild
4—moderate
5—moderate severe
6—severe
7—extreme The PANSS Individual subscales are described below.

P1. DELUSIONS—Beliefs which are unfounded, unrealistic and idiosyncratic.

P2. CONCEPTUAL DISORGANISATION—Disorganized process of thinking characterized by disruption of goal-directed sequencing, e.g., circumstantiality, loose associations, tangentiality, gross illogicality or thought block.

P3. HALLUCINATORY BEHAVIOUR—Verbal report or behaviour indicating perceptions which are not generated by external stimuli. These may occur in the auditory, visual, olfactory or somatic realms.

P4. EXCITEMENT—Hyperactivity as reflected in accelerated motor behaviour, heightened responsivity to stimuli, hypervigilance or excessive mood lability.

P5. GRANDIOSITY—Exaggerated self-opinion and unrealistic convictions of superiority, including delusions of extraordinary abilities, wealth, knowledge, frame, power and moral righteousness.

P6. SUSPICIOUSNESS/PERSECUTION—Unrealistic or exaggerated ideas of persecution, as reflected in guardedness, ad distrustful attitude, suspicious hypervigilance or frank delusions that others mean harm.

P7. HOSTILITY—Verbal and nonverbal expressions of anger and resentment, including sarcasm, passive-aggressive behavior, verbal abuse and assualtiveness.

N1. BLUNTED AFFECT—Diminished emotional responsiveness as characterized by a reduction in facial expression, modulation of feelings and communicative gestures.

N2. EMOTIONAL WITHDRAWAL—Lack of interest in, involvement with, and affective commitment to life's events.

N3. POOR RAPPORT—Lack of interpersonal empathy, openness in conversation and sense of closeness, interest or involvement with the interviewer. This is evidenced by interpersonal distancing and reduced verbal and nonverbal communication.

N4. PASSIVE/APATHETIC SOCIAL WITHDRAWAL—Diminished interest and initiative in social interactions due to passivity, apathy, anergy or avolition. This leads to reduced interpersonal involvements and neglect of activities of daily living.

N5. DIFFICULTY IN ABSTRACT THINKING—Impairment in the use of the abstract-symbolic mode of thinking, as evidenced by difficulty in classification, forming generalizations and proceeding beyond concrete or egocentric thinking in problem-solving tasks.

N6. LACK OF SPONTANEITY AND FLOW OF CONVERSATION—Reduction in the normal flow of communication associated with apathy, avolition, defensiveness or cognitive deficit. This is manifested by diminished fluidity and productivity of the verbal interactional process.

N7. STEREOTYPED THINKING—Decreased fluidity, spontaneity and flexibility of thinking, as evidenced in rigid, repetitious or barren thought content.

G1. SOMATIC CONCERN—Physical complaints or beliefs about bodily illness or malfunctions. This may range from a vague sense of ill being to clear-cut delusions of catastrophic physical disease.

G2. ANXIETY—Subjective experience of nervousness, worry, apprehension or restlessness, ranging from excessive concern about the present or future to feelings of panic.

G3. GUILT FEELINGS—Sense of remorse or self-blame for real or imagined misdeeds in the past.

G4. TENSION—Overt physical manifestations of fear, anxiety, and agitation, such as stiffness, tremor, profuse sweating and restlessness.

G5. MANNERISMS AND POSTURING—Unnatural movements or posture as characterized be an awkward, stilted, disorganized, or bizarre appearance.

G6. DEPRESSION—Feelings of sadness, discouragement, helplessness and pessimism.

G7. MOTOR RETARDATION—Reduction in motor activity as reflected in slowing or lessening or movements and speech, diminished responsiveness of stimuli, and reduced body tone.

G8. UNCOOPERATIVENESS—Active refusal to comply with the will of significant others, including the interviewer, hospital staff or family, which may be associated with distrust, defensiveness, stubbornness, negativism, rejection of authority, hostility or belligerence.

G9. UNUSUAL THOUGHT CONTENT—Thinking characterized by strange, fantastic or bizarre ideas, ranging from those which are remote or atypical to those which are distorted, illogical and patently absurd.

G10. DISORIENTATION—Lack of awareness of one's relationship to the milieu, including persons, place and time, which may be due to confusion or withdrawal.

G11. POOR ATTENTION—Failure in focused alertness manifested by poor concentration, distractibility from internal and external stimuli, and difficulty in harnessing, sustaining or shifting focus to new stimuli.

G12. LACK OF JUDGEMENT AND INSIGHT—Impaired awareness or understanding of one's own psychiatric condition and life situation. This is evidenced by failure to recognize past or present psychiatric illness or symptoms, denial of need for psychiatric hospitalization or treatment, decisions characterized by poor anticipation or consequences, and unrealistic short-term and long-range planning.

G13. DISTURBANCE OF VOLITION—Disturbance in the willful initiation, sustenance and control of one's thoughts, behavior, movements and speech.

G14. POOR IMPULSE CONTROL—Disordered regulation and control of action on inner urges, resulting in sudden, unmodulated, arbitrary or misdirected discharge of tension and emotions without concern about consequences.

G15. PREOCCUPATION—Absorption with internally generated thoughts and feelings and with autistic experiences to the detriment of reality orientation and adaptive behavior.

G16. ACTIVE SOCIAL AVOIDANCE—Diminished social involvement associated with unwarranted fear, hostility, or distrust.

Each patient's disease manifestation and process is unique. PANSS provides a structured, objective way of describing the various aspects of psychopathology of a given patient. However, proper implementation of the PANSS requires highly trained personnel to conduct the assessment and to interpret the results, and there is potential for site to site variability, especially outside the research setting.

Each of the PANSS composite scales and subscales can be considered a clinical endophenotype. The ability to link genetic profiles to these clinical endophenotypes changes as response to psychotic treatments, or severity of the diseases, will enable clinicians to refine a patient's diagnosis and develop a personalized therapeutic strategy for each patient. By identifying the genetic contributions to specific endophenotypes, the physician can create a personalized diagnosis and treatment regime for the patient.

Additionally, changes in PANSS or the Brief Psychiatric Rating Scale (BPRS), which is derived from PANSS, are often the primary measures of efficacy in clinical trials. Moreover, certain subscales and composite scores are also evaluated for change. For example, positive symptoms and negative symptoms are two composite scores that have clinical relevance.

V. Treatment of Psychotic Disorders

As described herein, the presence of a OPRP genetic signature described herein has been correlated with an altered response to a treatment, e.g., a pharmacological treatment. An altered response can be, for example, a positive response (i.e., an improvement in one or more symptoms of the disease), negative response (worsening of one or more symptoms of the disease), no response, or the presence or absence of side effects). Thus, the new methods can also include selecting or developing a treatment regimen for a subject determined to or suspected to have a psychotic disorder such as a psychotic disorder, based upon the absence or presence of a OPRP genetic signature.

For example, the inventors identified a OPRP genetic signature and developed its use in determining the optimal use of antipsychotic medications: i) Patients who are OPRP genetic signature negative have a higher probability of clinically significant improvement when treated with olanzapine when compared to patients who are OPRP genetic signature positive or untested. ii) Patients who are OPRP genetic signature negative may have a higher probability of clinically significant improvement when treated with olanzapine compared to other antipsychotic drugs. For example, this group responds better to olanzapine than to perphenazine, quetiapine, risperidone, or ziprasidone. iii) Patients who are OPRP genetic signature positive have a lower probability of clinically significant improvement when treated with olanzapine compared to similar patients who are OPRP genetic signature negative. Since olanzapine has a significant metabolic side effect burden compared to alternative first-line antipsychotics that demonstrate non-inferiority to olanzapine, it may be appropriate to recommend that first-line antipsychotics with lower metabolic side-effect burdens than olanzapine be used preferentially for OPRP genetic signature positive patients.

The methods can also include administering a selected treatment regimen to a subject having, or suspected to have a psychotic disorder such as a psychotic disorder, to thereby treat, prevent or delay further progression of the disease. A treatment regimen can include the administration of a selected antipsychotic medications to a subject identified as at risk of developing a psychotic disorder, before the onset of any psychotic episodes. The medications can be selected based on the absence of a OPRP genetic signature that is associated with, for example, good response, or the absence of significant side effects.

As used herein, the term "treat" or "treatment" is defined as the prescription, application or administration of a treatment regimen, e.g., a therapeutic agent or modality, to a subject, e.g., a patient. The subject can be a patient having a symptom of a psychotic disorder, or at risk of developing (i.e., a predisposition toward) such a disorder. The treatment can be to cure, heal, alleviate, relieve, alter, remedy, ameliorate, palliate, improve or affect a psychotic disorder, the symptoms of a psychotic disorder, or the predisposition toward a psychotic disorder.

The methods described herein, e.g., methods of determining a treatment regimen and methods of treatment or prevention of a psychotic disorder, can further include the step of monitoring the subject, e.g., for a change (e.g., an increase or decrease) in one or more of the diagnostic criteria for a psychotic disorder, listed herein, or any other parameter related to clinical outcome. The subject can be monitored in one or more of the following periods: prior to beginning of treatment; during the treatment; or after one or more elements of the treatment have been administered. Monitoring can be used to evaluate the need for further treatment with the same or a different therapeutic agent or modality. Generally, a decrease in one or more of the parameters described above is indicative of the improved condition of the subject, although with red blood cell and platelet levels, an increase can be associated with the improved condition of the subject.

The methods can be used, e.g., to evaluate the suitability of, or to choose between alternative treatments, e.g., a particular dosage, mode of delivery, time of delivery, inclusion of adjunctive therapy, e.g., administration in combination with a second agent, or generally to determine the subject's probable drug response genotype. The effects of the treatment or combination of treatments on each of these subjects can be used to determine if a treatment or combination of treatments is particularly effective on a sub-group of subjects having a psychotic disorder. In other embodiments, various treatments or combinations of treatments can be evaluated by administering two different treatments or combinations of treatments to at least two different subjects having a psychotic disorder, and a determined OPRP genetic signature status as described herein. Such methods can be used to determine if a particular treatment or combination of treatments is more effective than others in treating this subset of patients.

A. Current Treatments for Psychotic Disorders

Atypical antipsychotic drugs listed in order of current prescribing frequency for these disorders include: risperidone, quetiapine, olanzapine, aripiprazole, ziprasidone, clozapine, paliperidone, and iloperidone. Typical antipsychotic drugs include haloperidol, fluphenazine, perphenazine, and others (Meltzer and Bobo, 2009). Atypical antipsychotics are favored because of lower parkinsonian side effects and perceived greater efficacy. There are several long acting formulations of typical antipsychotic drugs, which are seldom used in the US. Among the atypical agents, only long acting, injectable risperidone, paliperidone and olanzapine are currently available; and others, e.g., long acting aripiprazole, are in development. These formulations are highly effective since they provide great help with regard to compliance, an enormous problem with both bipolar and schizophrenia patients. However, they are underutilized in the marketplace.

All of the antipsychotic medications have some degree of side-effects and other limitations. Metabolic side effects with some atypical antipsychotic drugs (weight gain, increased lipids, and problems with glucose regulation, including diabetes) exacerbate the discontinuation rates and limit overall effectiveness the implicated drugs. Olanzapine and clozapine, two of the most efficacious drugs for treating psychosis, have the greatest incidence of metabolic side-effects (Nasrallah, 2007).

Subjects with SZ typically require acute treatment for psychotic exacerbations, and long-term treatment including maintenance and prophylactic strategies to sustain symptom improvement and prevent recurrence of psychosis. Subjects with schizoaffective disorder experience the symptoms of both SZ and affective disorder (manic and/or depressive), thus require the specific treatments for each disorder. Subjects with SPD sometimes require medication for acute psychotic episodes but are often treated using psychosocial methods. The methods described herein can include the administration of one or more accepted or experimental treatment modalities to a person identified as having, suspected to have, or at risk of developing a psychotic disorder such as SZ, SPD, or a SD, based on the presence of a OPRP genetic signature status. Currently accepted treatments presently include both pharmacologic and psychosocial management, and occasionally electroconvulsive therapy (ECT).

Standard pharmacologic therapies for SZ and SD include the administration of one or more antipsychotic medications, which are typically antagonists acting at postsynaptic $D_2$ dopamine receptors in the brain. Antipsychotic medications include conventional, or first generation, antipsychotic agents, which are sometimes referred to as neuroleptics because of their neurologic side effects, and second generation antipsychotic agents, which are less likely to exhibit neuroleptic effects and have been termed atypical antipsychotics.

Standard pharmacologic therapies for SD also include the administration of a combination of antidepressant, and anti-anxiety medication. Suitable antidepressants include serotonergic antidepressants, e.g., fluoxetine or trazodone. Suitable anxiolytics include benzodiazepines, e.g., lorazepam, clonazepam. Lithium can also be administered. Thus, in some embodiments, the methods can include the administration of one or more antidepressant and/or anti-anxiety medications to a person identified as having or suspected to have SD in combination with a treatment plan based on OPRP genetic signature status.

The methods can also include psychosocial and rehabilitation interventions, e.g., interventions that are generally accepted as therapeutically beneficial, e.g., cognitive-behavioral therapy for treatment-resistant positive psychotic symptoms; supportive, problem-solving, educationally oriented psychotherapy; family therapy and education programs aimed at helping patients and their families understand the patient's illness, reduce stress, and enhance coping capabilities; social and living skills training; supported employment programs; and/or the provision of supervised residential living arrangements.

Currently accepted treatments for SZ are described in greater detail in the *Practice Guideline for the Treatment of Patients With Schizophrenia,* 2004, which is incorporated herein by reference in its entirety.

Currently accepted treatments for BD are described in greater detail in the *Treatment of Patients With Bipolar Disorder,* 2006, which is incorporated herein by reference in its entirety.

There are seven commonly prescribed atypical antipsychotic medications for bipolar disorder:

Abilify (aripiprazole)
Risperdal (risperidone)
Zyprexa (olanzapine)
Seroquel (quetiapine)
Geodon (ziprasidone)
Cloazril (clozapine)
Symbyax (olanzapine/fluoxetine)

The atypical antipsychotics have several significant side-effects, including weight gain, metabolic and hormonal dis-regulation, and sexual dysfunction. Weight gain, in particular, can be a significant issue as many people treated with atypical antipsychotics expect to gain weight, sometimes significantly so. Because weight gain is also associated with an increased risk for Type II diabetes, individuals taking an atypical antipsychotic should be carefully monitored by their physician. Other metabolic disturbances include elevated prolactin levels and altered steroid metabolism. Additionally, both men and women report significant levels of sexual dysfunction.

Drugs approved for the treatment of Bipolar disorder can have one or more indications, e.g., U.S. FDA (or other regulatory body) approved uses. Some of these indications include: Treatment of Acute Mania episodes; Bipolar Mania maintenance; Bipolar depression; Treatment of mixed mania and depression episodes.

Clinicians most commonly initiate treatment with oral risperidone, especially now that it is generic. Often, however, clinicians will switch patients to another drug after less than 1 to 6 months treatment. This common practice occurs based on what is perceived by patients and clinicians as both insufficient efficacy and unacceptable side effects, such as Parkinsonism, prolactin elevations or weight gain. Olanzapine, which was found to be the most effective treatment in the CATIE study and is closest in pharmacology to clozapine (the drug generally accepted to have the highest efficacy, particularly in treatment resistant subjects), is considered to be a highly effective agent (Meltzer and Bobo, 2009). Indeed, olanzapine became the most prescribed treatment and initial drug of choice after its introduction until concerns about metabolic side effects became evident (Meltzer, 2005). Metabolic side effects (weight gain, glucose dysregulation, lipid dysregulation and risk of diabetes) have greatly reduced the utilization of olanzapine despite its high efficacy.

B. Pharmacogenetic Testing

Clinicians currently have no way of knowing which drug is best for a specific patient other than from previous successful or unsuccessful trials. They make decisions based on their overall experience with a given drug as well as the influence of advertising and recommendations from clinic supervisors. Also options may be limited because, without a medical rationale, many states limit access to highly efficacious medications (primarily olanzapine) for Medicaid recipients due to cost concerns.

Payers would welcome a diagnostic test that enhances compliance and response rates for their clients. Compliance with oral antipsychotic drugs is a major problem, with 50% of patients ceasing to take them within 6 months of prescription, leading to relapse (return of psychosis) and hospitalization. While U.S. consumers and government agencies spend a considerable amount of money on atypical drugs, relapse and hospitalization represent the largest costs associated with schizophrenia and BP. Thus, reducing the rate of hospitalizations and relapse can lead to very significant cost savings and improved patient care.

It is consensus opinion among experts in the treatment of schizophrenia that a pharmacogenetic test which could deliver information that led to a more rapid and extensive control of psychosis would become the dominant driver of choice of medication options. Physicians could engage patients in a rational dialogue regarding treatment choice based on genetic profile. With this additional information, physicians and patients could make calculated risk-benefit analysis regarding potential efficacy and side-effect concerns of the various antipsychotic medications. There is also a published cost-effectiveness analysis which supports the value of pharmacogenetic testing (Perlis et al., 2005).

With regards to both prophylactic and therapeutic methods of treatment of psychotic disorders such as a psychotic disorder, such treatments may be specifically tailored or modified, based on knowledge obtained from the field of pharmacogenomics. "Pharmacogenomics," as used herein, refers to the application of genomics technologies such as structural chromosomal analysis, to drugs in clinical development and on the market. See, for example, Eichelbaum et al. (1996) and Linder et al. (1997). Specifically, as used herein, the term refers the study of how a patient's genes determine his or her response to a drug (e.g., a patient's "drug response phenotype," or "drug response genotype"). Thus, another aspect of the invention provides methods for tailoring an individual's prophylactic or therapeutic treatment according to that individual's drug response genotype, especially, a OPRP genetic signature status.

Information generated from pharmacogenomic research using a method described herein can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when administering a therapeutic composition, e.g., a cytotoxic agent or combination of cytotoxic agents, to a patient, as a means of treating or preventing psychotic disorders such as a psychotic disorder.

In one embodiment, a physician or clinician may consider applying knowledge obtained in relevant pharmacogenomics studies, e.g., using a method described herein, when determining whether to administer a pharmaceutical composition, e.g., an antipsychotic agent or a combination of antipsychotic agents, to a subject. In another embodiment, a physician or clinician may consider applying such knowledge when determining the dosage, e.g., amount per treatment or frequency of treatments, of a treatment, e.g., a antipsychotic agent or combination of antipsychotic agents, administered to a patient.

As one example, information regarding a genetic signature associated with an altered pharmacogenomic response for psychotic disorders as described herein, can be used to stratify or select a subject population for a clinical trial. The information can, in some embodiments, be used to stratify individuals that may exhibit a toxic response to a treatment from those that will not. In other cases, the information can be used to separate those that are more likely to be non-responders from those who will be responders. The OPRP genetic signature described herein can be used in pharmacogenomics-based design and to manage the conduct of a clinical trial, e.g., as described in U.S. Pat. Pub. No. 2003/0108938.

As another example, information regarding a OPRP genetic signature associated with an increased severity of psychotic disorders, or with altered pharmacogenomic response for psychotic disorders, as described herein, can be used to stratify or select human cells or cell lines for drug testing purposes. Human cells are useful for studying the effect of a polymorphism on physiological function, and for identifying and/or evaluating potential therapeutic agents for the treatment of psychotic disorders, e.g., anti-psychotics. Thus the methods can include performing the present methods on genetic material from a cell line. The information can, in some embodiments, be used to separate cells that respond particular drugs from those that do not respond, e.g. which cells show altered second messenger signaling.

C. Theranostics

As used herein, the word theranostic is a combination of a specific therapy and diagnostic. The combination represents the use of a diagnostic test to identify a specific patient sub-type(s) of psychotic disorders such as a psychotic disorder that have common genetic, clinical, metabolic, and/or prognostic features. By performing a diagnostic test, e.g. a genetic test to determine OPRP genetic signature, the physician or clinician can place the patient into a specific disease sub-type or category, for example, an OPRP genetic signature positive or negative subgroup. Moreover, patients in this sub-type respond to a given therapy in a particular manner.

Also included herein are compositions and methods for the identification and treatment of subjects who have an increased severity of a psychotic disorder, or altered clinical presentation of a psychotic disorder, such that a theranostic approach can be taken to test such individuals to determine the effectiveness of a particular therapeutic intervention (e.g., a pharmaceutical or non-pharmaceutical intervention as described herein) and/or to alter the intervention to enhance the effectiveness. Thus, the methods and compositions described herein provide a means of optimizing the treatment of a subject having or suspected to have a psychotic disorder such as SZ. Provided herein is a theranostic approach to treating and preventing a psychotic disorder such as SZ, by integrating diagnostics and therapeutics to improve the real-time treatment of a subject. Practically, this means creating tests that can identify which patients are most suited to a particular therapy, and providing feedback on how well a drug is working to optimize treatment regimens.

Within the clinical trial setting, a theranostic method or composition of the invention can provide key information to optimize trial design, monitor efficacy, and enhance drug safety. For instance, "trial design" theranostics can be used for patient stratification, determination of patient eligibility (inclusion/exclusion), creation of homogeneous treatment groups, and selection of patient samples that are representative of the general population. Such theranostic tests can therefore provide the means for patient efficacy enrichment, thereby minimizing the number of individuals needed for trial recruitment. "Efficacy" theranostics are useful for monitoring therapy and assessing efficacy criteria. Finally, "safety" theranostics can be used to prevent adverse drug reactions or avoid medication error.

The methods described herein can include retrospective analysis of clinical trial data as well, both at the subject level and for the entire trial, to detect correlations between a genetic signature as described herein and any measurable or quantifiable parameter relating to the outcome of the treatment, e.g., efficacy (the results of which may be binary (i.e., yes and no) as well as along a continuum), side-effect profile (e.g., weight gain, metabolic dysfunction, lipid dysfunction, movement disorders, or extrapyramidal symptoms), treatment maintenance and discontinuation rates, return to work status, hospitalizations, suicidality, total healthcare cost, social functioning scales, response to non-pharmacological treatments, and/or dose response curves. The results of these correlations can then be used to influence decision-making, e.g., regarding treatment or therapeutic strategies, provision of services, and/or payment. For example, a correlation between a positive outcome parameter (e.g., high efficacy, low side effect profile, high treatment maintenance/low discontinuation rates, good return to work status, low hospitalizations, low suicidality, low total healthcare cost, high social function scale, favorable response to non-pharmacological treatments, and/or acceptable dose response curves) and a OPRP genetic signature can influence treatment such that the treatment is recommended or selected based on the presence or absence of the OPRP genetic signature.

VI. Kits

Certain aspects of the present invention provides kits, such as diagnostic and therapeutic kits. Kits may comprise a container with a label. Suitable containers include, for example, bottles, vials, and test tubes. The containers may be formed from a variety of materials such as glass or plastic. The container may hold a composition which includes a probe or an array that could be used to determine a OPRP genetic signature, which could be effective for diagnostic or pharmacogenomic applications. The label on the container may indicate that the composition is used for a specific diagnostic or pharmacogenomic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

Within the scope of the invention are kits comprising a probe that hybridizes with a region of human chromosome as described herein and can be used to detect a polymorphism related to a OPRP genetic signature. The kit can include one or more other elements including: instructions for use; and other reagents, e.g., a label, or an agent useful for attaching a label to the probe. Instructions for use can include instructions for diagnostic applications of the probe for assessing severity of a psychotic disorder such as SZ in a method described herein. Other instructions can include instructions for attaching a label to the probe, instructions for performing in situ analysis with the probe, and/or instructions for obtaining a sample to be analyzed from a subject. As discussed above, the kit can include a label, e.g., any of the labels described herein. In some embodiments, the kit includes a labeled probe that hybridizes to a region of human chromosome as described herein, e.g., a labeled probe as described herein.

The kit can also include one or more additional probes that hybridize to the same chromosome, e.g., chromosome 2 or 5, or another chromosome or portion thereof that can have an abnormality associated with diagnostic applications. For example, the additional probe or probes can be: a probe that hybridizes to human chromosome 22q11-12 or a portion thereof, (e.g., a probe that detects a sequence associated with a psychotic disorder in this region of chromosome 22), or probes that hybridize to all or a portion of 22q12.3 (e.g., near D22S283), 22q11.2, 22q11.2, 22q11-q13, 1q42.1, 1q42.1, 1q21-q22, 2p, 2q, 3p25, 4p, 4q, 5q11.2-q13.3, 6p22.3, 6p23, 6q13-q26, 7q, 8p12-21, 8q, 9p, 10p15-p13 (e.g., near D10S189), 10q22.3, 11q14-q21, 12q24, 13q34, 13q32, 14q32.3, 15q15, 16p, 17q, 18p, 18q, 19p. 20p, 21q, Xq, and/or the X/Y pseudoautosomal region. A kit that includes additional probes can further include labels, e.g., one or more of the same or different labels for the probes. In other embodiments, the additional probe or probes provided with the kit can be a labeled probe or probes. When the kit further includes one or more additional probe or probes, the kit can further provide instructions for the use of the additional probe or probes.

Kits for use in self-testing can also be provided. For example, such test kits can include devices and instructions that a subject can use to obtain a sample, e.g., of buccal cells or blood, without the aid of a health care provider. For example, buccal cells can be obtained using a buccal swab or brush, or using mouthwash.

Kits as provided herein can also include a mailer, e.g., a postage paid envelope or mailing pack, that can be used to return the sample for analysis, e.g., to a laboratory. The kit can include one or more containers for the sample, or the sample can be in a standard blood collection vial. The kit can also include one or more of an informed consent form, a test requisition form, and instructions on how to use the kit in a method described herein. Methods for using such kits are also included herein. One or more of the forms, e.g., the test requisition form, and the container holding the sample, can be coded, e.g., with a bar code, for identifying the subject who provided the sample.

Kits may also comprise or be coupled to a system which can make recommendations and/or analysis of efficacy, risk or side effects for treatment of a psychotic disorder based on a determined OPRP genetic signature status. The system may comprise a server, a processor, or a tangible computer readable program product. For example, if the kit determines the presence or absence of an OPRP genetic signature, the system may perform an analysis and generate an efficacy and risk profile for treatment with a psychotic treatment, such as treating with olanzapine.

VII. Probes

Nucleic acid probes can be used to detect and/or quantify the presence of a particular target nucleic acid sequence within a sample of nucleic acid sequences, e.g., as hybridization probes, or to amplify a particular target sequence within a sample, e.g., as a primer. Probes have a complimentary nucleic acid sequence that selectively hybridizes to the target nucleic acid sequence. In order for a probe to hybridize to a target sequence, the hybridization probe must have sufficient identity with the target sequence, i.e., at least 70%, e.g., 80%, 90%, 95%, 98% or more identity to the target sequence, or any range derivable therein. The probe sequence must also be sufficiently long so that the probe exhibits selectivity for the target sequence over non-target sequences. For example, the probe will be at least 10, e.g., 15, 20, 25, 30, 35, 50, 100, 200, 300, 400, 500, 600, 700, 800, 900, or more nucleotides in length, or any range derivable therein. In some embodiments, the probes are not more than 30, 50, 100, 200, 300, 500, 750, or 1000 nucleotides in length, or any range derivable therein. Specifically, probes may be about 20 to about $1\times10^6$ nucleotides in length. Probes include primers, which generally refers to a single-stranded oligonucleotide probe that can act as a point of initiation of template-directed DNA synthesis using methods such as PCR (polymerase chain reaction), LCR (ligase chain reaction), etc., for amplification of a target sequence.

In some embodiments, the probe is a test probe, e.g., a probe that can be used to detect polymorphisms in a region described herein, e.g., SV2C or MGAT4C polymorphisms as described herein. In some embodiments, the probe can hybridize to a target sequence in complete linkage disequilibrium with one of the SNPs described herein for determination of an OPRP genetic signature.

In some embodiments, the probe can bind to another marker sequence associated with a psychotic disorder such as SZ as described herein.

Control probes can also be used. For example, a probe that binds a less variable sequence, e.g., repetitive DNA associated with a centromere of a chromosome, can be used as a control. Probes that hybridize with various centromeric DNA and locus-specific DNA are available commercially, for example, from Vysis, Inc. (Downers Grove, Ill.), Molecular Probes, Inc. (Eugene, Oreg.), or from Cytocell (Oxfordshire, UK). Probe sets are available commercially, e.g., from Applied Biosystems, e.g., the Assays-on-Demand SNP kits. Alternatively, probes can be synthesized, e.g., chemically or in vitro, or made from chromosomal or genomic DNA through standard techniques. For example, sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification via the polymerase chain reaction (PCR). See, for example, Nath and Johnson (1998); Wheeless et al. (1994); U.S. Pat. No. 5,491,224.

In some embodiments, the probes are labeled, e.g., by direct labeling, with a fluorophore, an organic molecule that fluoresces after absorbing light of lower wavelength/higher energy. A directly labeled fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, e.g., U.S. Pat. No. 5,491,224.

Fluorophores of different colors can be chosen such that each probe in a set can be distinctly visualized. For example, a combination of the following fluorophores can be used: 7-amino-4-methylcoumarin-3-acetic acid (AMCA), Texas Red™ (Molecular Probes, Inc., Eugene, Oreg.), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethyl-rhodamine-5-(and-6)-isothiocyanate, 5-(and-6)-carboxytetramethylrhodamine, 7-hydroxycoumarin-3-carboxylic acid, 6-[fluorescein 5-(and-6)-carboxamido]hexanoic acid, N-(4,4-difluoro-5,7-dimethyl-4-bora-3a,4a diaza-3-indacenepropionic acid, eosin-5-isothiocyanate, erythrosin-5-isothiocyanate, and Cascade™ blue acetylazide (Molecular Probes, Inc., Eugene, Oreg.). Fluorescently labeled probes can be viewed with a fluorescence microscope and an appropriate filter for each fluorophore, or by using dual or triple band-pass filter sets to observe multiple fluorophores. See, for example, U.S. Pat. No. 5,776,688. Alternatively, techniques such as flow cytometry can be used to examine the hybridization pattern of the probes. Fluorescence-based arrays are also known in the art.

In other embodiments, the probes can be indirectly labeled with, e.g., biotin or digoxygenin, or labeled with radioactive isotopes such as $^{32}P$ and $^{3}H$. For example, a probe indirectly labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

Oligonucleotide probes that exhibit differential or selective binding to polymorphic sites may readily be designed by one of ordinary skill in the art. For example, an oligonucleotide that is perfectly complementary to a sequence that encompasses a polymorphic site (i.e., a sequence that includes the polymorphic site, within it or at one end), such as rs2285162, rs2285166, or rs2285167, will generally hybridize preferentially to a nucleic acid comprising that sequence, as opposed to a nucleic acid comprising an alternate polymorphic variant.

VIII. Arrays and Uses Thereof

In another aspect, the invention features methods of determining the absence or presence of an OPRP genetic signature using an array described above. In a further aspect, the invention features arrays that include a substrate having a plurality of addressable areas, and methods of using them. At least one area of the plurality includes a nucleic acid probe that binds specifically to a sequence comprising a polymorphism such rs11960832 or rs7975477 and can be used to detect the absence or presence of said polymorphism, e.g., one or more SNPs, microsatellites, minisatellites, or indels, to determine an OPRP genetic signature. For example, the array can include one or more nucleic acid probes that can be used to detect a polymorphism such as rs11960832 or rs7975477. In some embodiments, the array further includes at least one area that includes a nucleic acid probe that can be used to specifically detect another marker associated with a psychotic disorder such as SZ as described herein. The substrate can be, e.g., a two-dimensional substrate known in the art such as a glass slide, a wafer (e.g., silica or plastic), a mass spectroscopy plate, or a three-dimensional substrate such as a gel pad. In some embodiments, the probes are nucleic acid capture probes.

Methods for generating arrays are known in the art and include, e.g., photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145). The array typically includes oligonucleotide probes capable of specifically hybridizing to different polymorphic variants. According to the method, a nucleic acid of interest, e.g., a nucleic acid encompassing a polymorphic site, (which is typically amplified) is hybridized with the array and scanned. Hybridization and scanning are generally carried out according to standard methods. See, e.g., Published PCT Application Nos. WO 92/10092 and WO 95/11995, and U.S. Pat. No. 5,424,186. After hybridization and washing, the array is scanned to determine the position on the array to which the nucleic acid hybridizes. The hybridization data obtained from the scan is typically in the form of fluorescence intensities as a function of location on the array.

Arrays can include multiple detection blocks (i.e., multiple groups of probes designed for detection of particular polymorphisms). Such arrays can be used to analyze multiple different polymorphisms. Detection blocks may be grouped within a single array or in multiple, separate arrays so that varying conditions (e.g., conditions optimized for particular polymorphisms) may be used during the hybridization. For example, it may be desirable to provide for the detection of those polymorphisms that fall within G-C rich stretches of a genomic sequence, separately from those falling in A-T rich segments.

Additional description of use of oligonucleotide arrays for detection of polymorphisms can be found, for example, in U.S. Pat. Nos. 5,858,659 and 5,837,832. In addition to oligonucleotide arrays, cDNA arrays may be used similarly in certain embodiments of the invention.

The methods described herein can include providing an array as described herein; contacting the array with a sample, e.g., a portion of genomic DNA that includes at least a portion of human chromosome 22, e.g., a region between and/or including SNPs for a SULT4A gene, and/or optionally, a different portion of genomic DNA, e.g., a portion that includes a different portion of human chromosomes 1, 2, 3, 4, 5, 6, 7, 8, 9, 10, 11, 12, 13, 14, 15, 16, 17, 18, 19, 20, 21 and/or 22, or another chromosome, e.g., including another region associated with a psychotic disorder, pharmacological response, and/or psychiatric endophenotypes, and detecting binding of a nucleic acid from the sample to the array. Optionally, the method includes amplifying nucleic acid from the sample, e.g., genomic DNA that includes a portion of a human chromosome described herein, and, optionally, a region that includes another region associated with a psychotic disorder, pharmacological response, and/or psychiatric endophenotypes, prior to or during contact with the array.

In some aspects, the methods described herein can include using an array that can ascertain differential expression patterns or copy numbers of one or more genes in samples from normal and affected individuals (see, e.g., Redon et al., 2006). For example, arrays of probes to a marker described herein can be used to measure polymorphisms between DNA from a subject having a psychotic disorder and control DNA, e.g., DNA obtained from an individual that does not have a psychotic disorder and has no familial risk factors for a psychotic disorder. Since the clones on the array contain sequence tags, their positions on the array are accurately known relative to the genomic sequence. Different hybridization patterns between DNA from an individual afflicted with a psychotic disorder such as SZ and DNA from a normal individual at areas in the array corresponding to markers in human chromosome 1, 2, 3, 4, 5, 6, 7, 8, 9, 10, 11, 12, 13, 14, 15, 16, 17, 18, 19, 20, 21 and/or 22 as described herein, and, optionally, one or more other regions associated with a psychotic disorder are indicative of a risk of SZ-spectrum disorders. Methods for array production, hybridization, and analysis are described, e.g., in Snijders et al. (2001); Klein et al. (1999); Albertson et al. (2003); and Snijders et al. (2002). Real time quantitative PCR can also be used to determine copy number.

IX. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Assigning OPRP Genetic Signature Status

Finished genotypes provided by others were used to establish OPRP genetic signature status using a simple and intuitive scoring method based on the genotypes of SNPs rs11960832 and rs7975477. A positive OPRP genetic signature comprises a homozygous genotype for the T allele at SNP marker rs11960832 [i.e., rs11960832(T)/rs11960832 (T) homozygosity] in combination with either a homozygous or heterozygous genotype for the T allele at marker rs7975477 [i.e., rs7975477(T)/rs7975477(T) homozygosity or rs7975477(T)/rs7975477(C) heterozygosity].

A. Genotyping Methodology

The inventors seek only to document the well established quality of the genotyping methodologies used for the Examples. Both the Affymetrix and Illumina platforms are widely used commercially available platforms. The technology behind both platforms has been included in CLIA-approved genotyping tests at the manufactures' own facilities and at third party providers.

The data from the inventors derived from a large scale genotyping project that used microarray-based whole genome SNP genotyping approaches. The project was performed by the CATIE study group using Affymetrix and Perlegen microarray platforms (Sullivan et al., 2008).

The inventors were provided finished genotype data and do not have access to raw data files such as .cel files. As described in the previous and present examples, genotypes provided by others were used to establish OPRP genetic signature status using a simple and intuitive scoring method for the presence of this genetic signature.

B. Genotype Determination in the CATIE Study

Details of the genotyping performed by the CATIE consortium, including their rigorous quality control procedures, are described elsewhere (Sullivan et al., 2008). Briefly, peripheral venous blood was collected, and genomic DNA was extracted from lymphocytes. Analyses were performed at Perlegen Sciences in its CLIA, GLP facility using two microarray genotyping systems. The first was the Affymetrix 500K "A" chipset (Nsp I and Sty I chips, Santa Clara, Calif.) used as specified by the manufacturer. Detailed description of the SNP detection methodology can be found in Affymetrix product documentation (available on the world wide web at www.affymetrix.com/products_services/arrays/specific/ 500k.affx). Secondly, Perlegen used a custom 164K chip. The genotype calling methodology and extensive quality control measures used by the CATIE study group are reported by Sullivan and coworkers (Sullivan et al., 2008) and further described in detail in the supplemental technical material provided by the CATIE consortium (Sullivan et al., 2009).

As an example of the level of quality control used, the CATIE group performed duplicate analysis on 36 samples. The proportion of SNPs with non-missing genotype calls that disagreed in these duplicated samples was 0.00291. As an additional control, 277 individuals were genotyped at a second facility using a different SNP-calling algorithm to investigate potential site bias. Only 0.73% of called genotypes differed between the two sites.

C. Frequency of the OPRP Genetic Signature

Table 1 summarizes the observed frequencies for the OPRP Genetic Signature in Caucasians and African Americans.

TABLE 1

OPRP Genetic Signature Frequency

| Population | Approximate Frequency % |
|---|---|
| Caucasian | 6.5 |
| African American | 23.5 |

D. Using SNP Genotypes to Determine OPRP Genetic Signature Status

For the SNPS available in the CATIE study, OPRP genetic signature status is determined based on the genotype of the SNPs, SNPs rs11960832(T or C) and rs7975477(T or C). Patients are designated as OPRP genetic signature positive or negative using the simple scoring method illustrated in Table 2. As can be seen, only two of the nine possible genotype combinations result in a positive OPRP genetic signature status for an individual. Note that, OPRP genetic signature status can be assigned unambiguously in each case and that OPRP positive and negative statuses are mutually exclusive for any given individual who will carry a total of two and only two alleles for each of the two SNPs.

TABLE 2

Assignment OPRP Genetic Signature Based on SNP Genotypes

| rs11960832 | rs7975477 | OPRP Status |
|---|---|---|
| T/T | T/T | Positive |
| T/T | T/C | Positive |
| T/T | C/C | Negative |
| T/C | T/T | Negative |
| T/C | T/C | Negative |
| T/C | C/C | Negative |
| C/C | T/T | Negative |
| C/C | T/C | Negative |
| C/C | C/C | Negative |

The genetic signature scoring can be automated in Microsoft Excel by combining a series of logical arguments. For purposes of illustration, samples of the scoring by the Excel spreadsheet are reproduced below (Table 3). The example is not intended to be exhaustive. Failed genotypes, which are rare, are coded as question marks and result in "NO" designation in column "D". Column "G" provides the genetic signature status with a blank cell indicating genotyping failure that requires retesting.

TABLE 3

Sample Output for OPRP Genetic Signature calling Excel Spreadsheet

| A Sample ID | B rs11960832 | C rs7975477 | D Callable? | E Genotype | F Positive status call possible? | G OPRP Status |
|---|---|---|---|---|---|---|
| 1 | T_T | T_T | YES | T_T T_T | Yes | Positive |
| 2 | T_T | T_C | YES | T_T T_C | Yes | Positive |
| 3 | T_T | C_C | YES | T_T C_C | Yes | Negative |
| 4 | T_C | T_T | YES | T_C T_T | Yes | Negative |
| 5 | T_C | T_C | YES | T_C T_C | Yes | Negative |
| 6 | T_C | C_C | YES | T_C C_C | Yes | Negative |
| 7 | C_C | T_T | YES | C_C T_T | Yes | Negative |
| 8 | C_C | T_C | YES | C-C T_C | Yes | Negative |
| 9 | C_C | C_C | YES | C_C C-C | Yes | Negative |
| 10 | ? | ? | NO | ? | No | |
| 11 | T_T | ? | NO | T_T ? | No | |
| 12 | ? | T_T | NO | ? T_T | No | |

In summary, once genotyping has been performed for rs11960832 and rs7975477 (or markers in complete linkage disequilibrium with each of these), OPRP genetic signature status can be assigned using a simple and intuitive scoring method. This method is easily automated using logical functions in programs such as Microsoft Excel.

Example 2

The OPRP Genetic Signature Predicts Poor Response to Olanzapine

The CATIE study, a large federally funded clinical trial designed to assess the efficacy of antipsychotics in a real world setting, is a valuable resource for determining the role of genes in baseline psychopathology and drug response (Lieberman et al., 2005; Stroup et al., 2003). As part of the CATIE trial, detailed clinical evaluations were conducted, including Positive and Negative Syndrome Scale (PANSS) measurements at multiple time points, cognitive evaluation, vital signs, blood chemistry results, and drug response data. Additionally, whole genome SNP genotyping was performed for roughly half of the trial participants (Sullivan et al., 2008).

The inventors used samples collected in the course of the CATIE trial to study genetic signatures to determine if a genetic signature might contribute to the clinical differences in response to olanzapine. The inventors contemplated that a combination of one or more commonly occurring genetic variants (SNPs) might account for the poor response to olanzapine displayed by some patients.

A. Data and Methods Relating to the CATIE Sample

Genotype and phenotype data for the CATIE trial were recently made available to qualified researchers through the NIMH Center for Collaborative Genetic Studies on Mental Disorders. The sample consisted of a total of 738 patients. For the present study, the inventors assigned OPRP status to 628 subjects, including 411 subjects of self-reported European ancestry and 217 subjects of self-reported African ancestry. Further details on the patient population are described in the study by Sullivan and coworkers (Sullivan et al., 2008). The CATIE SNP genotype data evaluated included a total of 492,900 SNPs located throughout the genome.

The design of the CATIE study has been described in detail by others (Lieberman et al., 2005; Stroup et al., 2003). Briefly, 1460 subjects were randomly assigned one of several antipsychotics and those who did not respond or who chose to quit their current medication were re-randomized to another drug. Subjects that failed Phase 1 treatment with the typical antipsychotic perphenazine were treated differently than those subjects that failed phase I treatment with an atypical antipsychotic. Instead of entering into Phase II of the trial, subjects who switched from perphenazine entered Phase IB. For Phase IB, subjects were randomly assigned to an atypical antipsychotic—olanzapine, quetiapine or risperidone. Subjects who failed Phase IB then entered Phase II.

A total of 738 subjects consented to provide DNA for genetic study. Details regarding SNP genotyping and quality control have been recently published (Sullivan et al., 2008). Only retrospective genetic analyses, judged to be exempt from human studies requirements by an IRB, were conducted in the current study. For the genetic analyses presented herein, the inventors combined and evaluated drug response data for both Phase I and Phase IB of the CATIE study. All tested patients were studied using well established clinical endpoints comparing baseline, intermediate, and last observation carried forward (LOCF) for the PANSS scores using CATIE data. LOCF analysis is a commonly used clinical endpoint for clinical trials for neuropsychiatric drugs, with particular changes in PANSS scores being used to indicate clinically significant response (Leucht et al., 2009).

Using the clinical data from the CAIE trial, the inventors derived several different metrics used for quantifying response in clinical trials of antipsychotic medications. The most commonly used psychometric instrument is the Positive and Negative Syndrome Scale (PANSS), a 30-item semi-quantitative instrument scored by clinical professionals (Kay et al., 1987). The greater the decrease in PANSS score, the better the clinical response. The most direct measure of clinical response is absolute change in PANSS score. In addition to absolute change, the improvement is often reported as a percentage change from baseline PANSS score.

For example, many drug trials for antipsychotic medications report response as quantitative changes in PANSS score (Leucht et al., 2009). This approach is particularly useful for trials with active comparators or in cases where claims of drug superiority or non-inferiority are important (i.e. where relative improvement in symptoms is a key factor).

Alternatively the percentage change in PANSS may be used to derive a categorical definition of response, wherein subjects who meet a certain critical threshold of change are classified as responders and those that do not meet that criterion are classified as non-responders. For example, a decrease of at least 10% in total PANSS may be used as a threshold for response (Leucht et al., 2009).

Both approaches shed light on the clinical utility of the OPRP Genetic Signature as a biomarker, so the inventors presented results for both categorical definitions of response and for quantitative changes in percent PANSS.

B. Methods for Initial Genetic Signature Discovery and Characterization

To examine the relationship of genotypes to drug response the inventors used the publicly available PLINK software (Purcell et al., 2007; available on the world wide web at pngu.mgh.harvard.edu/purcell/plink/) and Helix tree (Version 6.4.1; Golden Helix, Bozeman, Mont.). The inventors used Last observation Carry Forward (LOCF) delta PANSS values as a measure of response to antipsychotic treatment. The inventors identified the TT genotype of SNP marker rs11960832 as a predictor of poor olanzapine response. The inventors refined the test further by conducting association analysis on using only those subjects that comprised the TT genotype of rs11960832. This further analysis enabled the authors to refine the test to include genotypes at SNP marker rs7975477. Presence of the TT or TC genotypes of rs7975477 in individuals that comprised the TT genotype at rs11960832 indicates OPRP positive status. The addition of the second SNP improved the utility of the test by enabling the test to work on all ethnicities.

C. The OPRP Genetic Signature Predicts Response to Antipsychotics Based on Quantitative Change in PANSS Score As mentioned previously, the mean change in absolute or percent PANSS provides an important measure of efficacy in patients undergoing antipsychotic treatments. Indeed, many pivotal trials in the psychosis field used absolute and/or percentage change in PANSS Score as the primary endpoint (Leucht et al., 2009). The performance of the investigational drug is then compared with placebo and/or an active comparator. Therefore, in addition to examining a categorical definition of clinically significant response, the inventors determined the impact of segmentation by OPRP genetic signature status on the quantitative measure of clinical improvement—delta PANSS for LOCF.

Table 4 shows the means and standard deviations (SD) for the percent change in PANSS for each of the drug arms segmented by OPRP Genetic Signature status for the CATIE study. A more negative number represents a greater degree of improvement. As can be seen from Table 4, the OPRP positive group responded significantly worse to olanzapine than did the OPRP negative group (+4.3% worse vs. −11.6% better, P=0.000001). OPRP positive patients responded more poorly to olanzapine than to any of the other antipsychotics individually or as a group. In contrast, OPRP negative patients responded well to olanzapine, with the response to olanzapine for this group of patients being statistically superior to response to perphenazine (P<0.001), to quetiapine (P<0.00001), to ziprasidone (P<0.00001), and to risperidone (P<0.05), as well as to all other drugs combined (+++++ P<0.00001).

TABLE 4

Change in PANSS Values for the CATIE Study

| | OPRP Positive | | | OPRP Negative | |
|---|---|---|---|---|---|
| Drug | N | DELTA PANSS %$^a$ | SD$^b$ | N | DELTA PANSS %$^a$ | SD$^b$ |
| Olanzapine | 26 | 4.3 | 10.5 | 139 | −11.6 | 15.3* |
| Perphenazine | 12 | −7.7^ | 20.1 | 110 | −4.2+++ | 17.8 |
| Quetiapine | 18 | −1.2 | 20.7 | 147 | −3.2++++ | 16.8 |
| Risperidone | 20 | −4.2^ | 16.1 | 146 | −6.4+ | 18.2 |
| Ziprasidone | 11 | −0.5 | 9.5 | 69 | −1.5++++ | 14.4 |
| All Drugs | 87 | −1 | 15.9 | 611 | −5.9 | 17.4 |
| All Drugs - except olanzapine | 61 | −3^ | 17 | 472 | −4.2++++ | 17.6 |

$^a$Mean change in PANSS score from baseline to LOCF
$^b$Standard deviation of the mean
*P = 0.000001 olanzapine OPRP positive performed worse than OPRP negative
^P < 0.05 olanzapine treated OPRP positive subjects responded significantly worse than OPRP positive subjects treated with other drugs
+P < 0.05, and ++P < 0.01 +++P < 0.001, and ++++P < 0.00001 olanzapine treated OPRP negative subjects responded significantly better than OPRP negative subjects treated with other drugs Another way to consider the response of the various groups is to analyze the difference in the mean PANSS changes. Table 5 compares various olanzapine treated OPRP positive subjects to various drug-OPRP groups. The positive mean differences between the groups indicate poorer response for the olanzapine treated OPRP positive patients. Additionally, the effect size (mean difference/standard deviation of pooled sample) is included in this table. The importance of the effect size will be discussed in the next section. For now, however, take note that the some effect sizes are greater than or equal to 0.5 suggesting the biomarker is identifying important differences in treatment response.

TABLE 5

Relative Response of Olanzapine-Treated OPRP Positive Subjects Compared to Other Groups in CATIE

| Comparison - Olanzapine OPRP+ | Mean difference[1] (95% CI) | Effect size[2] | P-Value[3] |
|---|---|---|---|
| Vs risperidone OPRP+ | 8.4 (0.6 to 16.4) | 0.6 | 0.03 |
| Vs perphenazine OPRP+ | 12 (2.0 to 22.0) | 0.7 | 0.02 |
| Vs quetiapine OPRP+ | 5.5 (−4.1 to 15.0) | 0.3 | 0.25 |
| Vs ziprasidone OPRP+ | 4.8 (−2.7 to 12.3) | 0.2 | 0.19 |
| Vs OPRP+ except olanzapine | 7.3 (0.1 to 14.5) | 0.5 | 0.03 |
| Vs olanzapine OPRP− | 15.9 (9.7 to 22.1) | 1.0 | 0.000001 |

[1]Mean difference calculated by subtracting the mean delta PANSS of the comparator group from the mean DELTA PANSS of the olanzapine treated OPRP positive (+) group
[2]Effect size is calculated by dividing the mean difference by the standard deviation
[3]P-value calculated using the T-test for comparison of 2 means D. Categorical Responder/Nonresponder Statistics Based on OPRP Genetic Signature As described above CATIE patients were studied using well established clinical endpoints comparing baseline, intermediate, and last observation carried forward (LOCF) for the PANSS scores. LOCF analysis is a commonly used clinical endpoint for clinical trials for neuropsychiatric drugs, with changes in PANSS scores of negative 10% being used as a possible endpoint to indicate clinically significant response (Leucht et al., 2009).

As summarized in Table 6, when patients are segmented by OPRP genetic signature status and treatment arm, olanzapine-treated OPRP positive subjects demonstrated a lesser likelihood of achieving a 10% PANSS decrease than any other group in CATIE.

TABLE 6

Relationship of OPRP Status to Drug Response in CATIE

| | OPRP Positive[a] | | | OPRP Negative[a] | | |
|---|---|---|---|---|---|---|
| Drug | ≦−10% | ≧−10% | Responders | ≦−10% | ≧−10% | Responders |
| Olanzapine | 1 | 25 | 4%* | 73 | 66 | 53%* |
| Risperidone | 7 | 12 | 35%^ | 55 | 91 | 38%+ |
| Quetiapine | 4 | 14 | 22%^ | 48 | 99 | 33%+++ |
| Perphenazine | 5 | 7 | 42%^^ | 39 | 71 | 35%+ |
| Ziprasidone | 2 | 9 | 18% | 16 | 53 | 23%++++ |
| All Drugs | 19 | 68 | 22% | 231 | 380 | 38% |
| All Except Olanzapine | 18 | 42 | 30%^^ | 158 | 314 | 33%++++ |

[a]Numbers of individuals showing the specified percent change in total PANSS (LOCF). A greater response corresponds to a more negative change in PANSS score, with individuals showing a change in PANSS of ≦−10% being categorized as responders
*P = 0.000002 olanzapine OPRP positive performed worse than OPRP negative
^P < 0.05, ^^P < 0.01 olanzapine treated OPRP positive subjects responded significantly worse than OPRP positive subjects treated with other drugs
+P<0.05, and ++P<0.01 +++P<0.001, and ++++P<0.0001 olanzapine treated OPRP negative subjects responded significantly better than OPRP negative subjects treated with other drugs.

Several points may be made regarding the data it Table 6. First, OPRP positive patients have a statistically lower probability of experiencing a clinical response using olanzapine therapy when compared to patients who are OPRP negative (P=0.000002). Second, OPRP positive patients have a lower probability of experiencing a clinically significant response using olanzapine when compared to all other antipsychotic drugs combined (P<0.01) or when compared specifically to risperidone (P<0.05) or to perphenazine (P<0.01). Third, OPRP negative patients respond better to olanzapine than to any of the other antipsychotics individually or as a group. Therefore, based on clinical improvement, OPRP positive patients are a subset of patients who are particularly poor candidates for olanzapine treatment, while OPRP negative are a subset of patients who respond particularly well to olanzapine.

The inventors also examined the impact of the OPRP status on whether patients' symptoms actually got worse when treated with olanzapine. This is an important safety consideration for antipsychotic drugs response, and failure of a drug to display the desired clinical response on a specific subset of patients could impact the drug label, being contraindicated for a particular subset of patients (see Example 5: "Risk Management Involving the OPRP Genetic Test). As summarized in Table 7, when patients are segmented by OPRP status and treatment arm, olanzapine-treated OPRP positive subjects demonstrated a greater likelihood of displaying a worsening of symptoms (LOCF delta PANSS≧0%) than any other group in CATIE.

TABLE 7

Relationship of OPRP Status to Worsening Symptoms in CATIE

| | OPRP Positive[a] | | | OPRP Negative[a] | | |
|---|---|---|---|---|---|---|
| Drug | ≧0% | ≦0% | Worsening | ≧0% | ≦0% | Worsening |
| Olanzapine | 18 | 8 | 69% | 26 | 113 | 19%* |
| Risperidone | 7 | 13 | 35%^ | 55 | 91 | 38%+++ |
| Quetiapine | 9 | 9 | 50% | 62 | 95 | 42%+++ |
| Perphenazine | 3 | 9 | 25%^ | 45 | 65 | 41%+++ |
| Ziprasidone | 4 | 7 | 36% | 34 | 35 | 49%++++ |
| All Drugs | 41 | 46 | 47% | 222 | 389 | 36% |
| All Except Olanzapine | 23 | 38 | 38%^^ | 196 | 286 | 41%++++ |

[a]Numbers of individuals showing the specified percent change in total PANSS (LOCF). Worsening of symptoms corresponds to an increase in PANSS score, with individuals showing a delta PANSS of ≧0% being categorized as having worsening symptoms.
*P = 0.0000007 olanzapine OPRP positive performed worse than OPRP negative
^P < 0.05, ^^P < 0.01 significantly more olanzapine treated OPRP positive subjects displayed worsening of symptoms than OPRP positive subjects treated with other drugs.
+P < 0.05, and ++P < 0.01 +++P < 0.001, and ++++P < 0.0001 significantly fewer olanzapine treated OPRP negative subjects displayed worsening of symptoms than OPRP negative subjects treated with other drugs.

Several points may be made regarding the data it Table 7. First, OPRP positive patients have a statistically higher probability of experiencing a worsening of symptoms using olanzapine therapy when compared to patients who are OPRP negative (P=0.0000007). Second, OPRP positive patients have a higher probability of experiencing a worsening symptoms using olanzapine when compared to all other antipsychotic drugs combined (P<0.01) or when compared specifically to risperidone (P<0.05) or to perphenazine (P<0.05). Third, OPRP negative patients have a significantly lower probability of displaying worsening symptoms when treated with olanzapine than when treated with any of the other antipsychotics individually or as a group. Therefore, based on worsening symptoms, OPRP positive patients are a subset of patients who are particularly poor candidates for olanzapine treatment, while OPRP negative are a subset of patients who respond particularly well to olanzapine.

In summary, the results for the CATIE study show that the ORRP genetic signature can be used to define subsets of patients that respond differently to antipsychotic medications. OPRP positive subjects, when treated with olanzapine, respond poorly and are at elevated risk of experiencing a worsening of symptoms as compared to either OPRP negative subjects treated with olanzapine or to OPRP positive subjects treated with other antipsychotics. In contrast OPRP negative patients respond particularly well to olanzapine and are at decreased risk of experiencing a worsening of symptoms as compared to either OPRP positive subjects treated with olanzapine or to OPRP negative subjects treated with other antipsychotics.

Example 3

Clinical Utility of the Biomarker

The primary rationale for determining the OPRP status of a patient is to alter medical practice in some manner. Currently in the psychiatric space, physicians lack useful tools to help them select the most efficacious antipsychotic medication for individual patients. All of the currently approved antipsychotics demonstrated superiority to placebo for treating psychotic symptoms as part of their approval process at the FDA. Examples of comparative effectiveness can be found in any New Drug Approval, e.g. the olanzapine approval package (Zyprexa (olanzapine) Approval Package NDA 20-592. FDA, Center for Drug Evaluation and Research 1996 Available from: world wide web via accessdata.fda.gov/drugsatfda_docs/nda/96/020592_Original_Approval_Pkg%20.pdf). However, a recently published meta-analysis of registration quality clinical trials showed only modest improvements over placebo.

Table 8 shows the results for the atypical antipsychotics used in the CATIE study. These drugs had effect sizes ranging from −0.42 to −0.59. The effect size is defined as the difference in the mean response for each drug minus the change in the placebo arm, divided by the standard deviation. In this case, a negative number means a greater improvement in psychopathology, i.e. a greater reduction in PANSS. For comparison, the same metrics are provided for olanzapine-treated OPRP positive patients compared to various other OPRP-drug combinations from the CATIE study. The effect size of the latter ranged from 0.2 to 1.0. To place this in context, the effect size for olanzapine treated OPRP positive vs. negative patients in CATIE was roughly 60% larger and in the opposite direction (1.0 vs. −0.59) than the effect size seen when comparing olanzapine to placebo for a population not segment by OPRP status.

TABLE 8

Comparative Effect Sizes of Atypical Antipsychotics vs. Placebo and First Generation Antipsychotics

| Drug | Number of Studies | Effect Size vs. Placebo[c] | Effect Size vs. FGA[d] | CATIE Effect Size |
|---|---|---|---|---|
| Olanzapine | 6 | −0.59 | −0.21 | 1.0[a] |
| Quetiapine | 5 | −0.42 | 0.01 | 0.3[b] |
| Risperidone | 7 | −0.59 | −0.25 | 0.6[b] |
| Ziprasidone | 4 | −0.48 | −0.04 | 0.2[b] |

[a]Olanzapine OPRP positive versus olanzapine OPRP negative
[b]Olanzapine OPRP positive versus drug OPRP positive
[c]Leucht et al. (2009)
[d]FGA = first generation antipsychotics. Results from Davis et al. (2003).

Currently, clinical practice emphasizes the increased efficacy of atypical antipsychotics over typical antipsychotics. Another meta-analysis examined the efficacy advantage of atypical antipsychotics compared to first generation, or typical, antipsychotics. This analysis revealed a very minor advantage for some of the atypical antipsychotics over typical antipsychotics, with effect sizes ranging from −0.25 to 0.01. Only olanzapine and risperidone showed a significant advantage in the meta-analysis. The effect sizes due to OPRP status for olanzapine (OPRP+ vs. OPRP−) or for olanzapine vs. other drugs after segmentation by OPRP status are up to four times as large as those seen when comparing olanzapine or risperidone to first generation antipsychotics in the meta-analysis. Based on these findings, a pharmacogenetic test for OPRP status could offer physicians a tool to identify a sub-population, OPRP positive subjects, for which there is a treatment option(s) that provides twice, or more, the efficacy advantage over olanzapine than the advantage currently observed by atypical over typical antipsychotics.

Another recent meta-analysis compared the effectiveness of the various atypical antipsychotics to each other. This study used the weighted mean difference in PANSS score (absolute not percent difference). Olanzapine consistently showed modest superiority to quetiapine, risperidone, and Ziprasidone, as shown in Table 9. However, this modest increase in efficacy in the unsegmented population is much smaller than the efficacy improvement observed for OPRP negative subjects treated with olanzapine in the CATIE sample. Conversely, the OPRP positive subjects treated with olanzapine displayed inferior response compared to other antipsychotics, in contrast to the results in the unsegmented population. Thus the a positive OPRP genetic signature identifies a special population for which the currently accepted paradigm of olanzapine having superior efficacy is inaccurate.

TABLE 9

Mean Difference Between Olanzapine and Other Atypical Antipsychotics[a]

| Olanzapine vs. | Meta-analysis[b] | CATIE unsegmented | CATIE OPRP[b]+ | CATIE OPRP− |
|---|---|---|---|---|
| Risperidone | −1.9 (−3.3 to −0.6) | −3.5 | 8.4 | −5.2 |
| Quetiapine | −3.7 (−5.4 to −1.9) | −6.2 | 5.5 | −8.4 |
| Ziprasidone | −8.3 (−11.0 to −5.6) | −4.9 | 4.8 | −10.1 |

[a]Negative values indicate that olanzapine displayed superior efficacy, and positive values indicate that olanzapine displayed inferior efficacy (measured in delta PANSS).
[b]Mean (95% CI) see Leucht et al. (2009)

In conclusion, segmentation by OPRP status identifies a sub-population, OPRP positive patients, that demonstrates inferior response to olanzapine. Conversely, OPRP negative patients show more improvement when treated with olanzapine than do OPRP positive subjects. Finally, for the OPRP negative patients, olanzapine demonstrates enhanced superiority over other medications based on meta-analysis for patient populations not segmented by OPRP status.

Example 4

Diagnostic Performance Using Categorical Definitions of Response

Several different measures of diagnostic performance can be used for comparing dichotomous outcomes. Two important metrics include percent positive agreement (PPA), a substitute for sensitivity, and percent negative agreement (PNA), a substitute for specificity. Tables 10 presents these measures of diagnostic performance along with the diagnostic odds ratio (DOR) for prediction of worsening of symptoms in CATIE for olanzapine treatment of OPRP positive patients compared to other groups.

TABLE 10

Diagnostic Performance of the OPRP Test in the CATIE Study For Worsening Symptoms (Delta PANSS ≧ 0)

| Comparison[a] | Worsen | Non-Worsen | PPA[b] (95% CI) | PNA[c] (95% CI) | DOR[d] (95% CI) |
|---|---|---|---|---|---|
| Olanzapine+ | 18 | 8 | 0.41 (0.28 to 0.56) | 0.93 (0.87 to 0.97) | 9.85 (3.8 to 25) |
| Olanzapine− | 26 | 113 | | | |
| Olanzapine+ | 18 | 8 | 0.86 (0.65 to 0.95) | 0.53 (0.31 to 0.74) | 6.75 (1.4 to 32) |
| Perphenazine+ | 3 | 9 | | | |
| Olanzapine+ | 18 | 8 | 0.67 (0.48 to 0.81) | 0.53 (0.31 to 0.74) | 2.25 (0.65 to 7.8) |
| Quetiapine+ | 9 | 9 | | | |
| Olanzapine+ | 18 | 8 | 0.72 (0.52 to 0.86) | 0.62 (0.541 to 0.79) | 4.17 (1.20 to 14.4) |
| Risperidone+ | 7 | 13 | | | |
| Olanzapine+ | 18 | 8 | 0.782 (0.61 to 0.93) | 0.57 (0.25 to 0.70) | 3.94 (0.89 to 17.4) |
| Ziprasidone+ | 4 | 7 | | | |

[a]A plus sign indicates OPRP positive and a negative sign indicates OPRP negative
[b]Percent Positive Agreement = (true positive)/(true positive + false negative) = OPRP positive olanzapine worsen/all worsen.
[c]Percent Negative Agreement = (true negative)/(true negative + false positive) = OPRP negative non-worsen for comparator/all non-worsen
[d]Diagnostic Odds Ratio − (True positive * true negative)/(False positive * false negative)

Example 5

Risk Management Involving OPRP Test

The OPRP test, as well as any test including an OPRP determination, will be used in the risk-benefit analysis for prescribing atypical antipsychotics—olanzapine in particular. The highly variable efficacy of olanzapine and moderate to large side effect burden create an opportunity to greatly enhance patient care and usefulness of olanzapine when combined with the OPRP test.

The risk management program (exemplified in FIG. 1) has the potential of becoming an FDA-mandated safety program for prescribing olanzapine vs. other antipsychotics. By incorporating the OPRP genetic signature determination into an electronic data exchange that interfaces with physicians, pharmacies labs and patients, this invention may be applied to guide all of the four groups involved in selection of and dispensing of olanzapine utilizing information that will optimize potential therapeutic benefits (such as optimal efficacy and improvement of symptoms) and minimize potential risks (such as lack of drug effect and risks associated with lack of drug effect like hospitalization and worsening of symptoms).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,683,202
U.S. Pat. No. 5,143,854
U.S. Pat. No. 5,288,514
U.S. Pat. No. 5,288,644
U.S. Pat. No. 5,384,261
U.S. Pat. No. 5,424,186
U.S. Pat. No. 5,491,224
U.S. Pat. No. 5,510,270
U.S. Pat. No. 5,527,681
U.S. Pat. No. 5,776,688
U.S. Pat. No. 5,837,832
U.S. Pat. No. 5,858,659
U.S. Patent Publn. 2003/0108938
U.S. Patent Publn. 2004/0014095
Albertson et al., *Breast Cancer Res. Treat.*, 78:289-298, 2003.
Alderborn et al., *Genome Research*, 10(8):1249-1258, 2000.
American Psychiatric Association. Diagnostic and Statistical Manual of Mental Disorders, 4th Ed., Washington, D.C.: American Psychiatric Association, 1994.
Ausubel et al., In: *Current Protocols in Molecular Biology*, John Wiley & Sons, NY, 631-636, 2003.
Baker et al., *Biol. Psychiatry*, 58(1):23-31, 2005.
Cadenhead, *Psychiatric Clinics of North America*, 25(4):837-53, 2002.
Callicott et al., *Proc. Natl. Acad. Sci. USA*, 102(24):8627-32. 2005.
Cannon et al., *Arch. Gen. Psychiatry*, 62(11):1205-13, 2005.
Chen et al., *Genome Research*, 9(5):492-498, 1999.
Church and Gilbert, *Proc. Natl. Acad. Sci. USA*, 81:1991-1995, 1988.
Cotton et al., *Proc. Natl. Acad. Sci. USA*, 85:4397-4401, 1985.
Davis et al, *Arch. Gen. Pysch.*, 60:553-564, 2003
Diagnostic and Statistical Manual of Mental Disorders, Fourth Edition, Text Revision, American Psychiatric Association, 2000.
Eckert et al., *PCR Methods and Applications*, 1(1):17-24, 1991.
Eichelbaum et al., *Clin. Exp. Pharmacol. Physiol.*, 23:983-985. 1996.
Flavell et al., *Cell*, 15:25, 1978.
Furukawa et al., *J. Hum. Genet.*, 44:397-401, 1999.
Geever et al., *Proc. Natl. Acad. Sci. USA*, 78:5081, 1981.
Gornick et al., *J. Autism Dev. Disord.*, 1-8, 2005.
Gothelf et al., *Nat. Neurosci.*, 8(11):1500-2, 2005.
Gottesman and Gould, *Amer. J. Psychiatry*, 160(4):636-45, 2003.
Guatelli et al., *Proc. Nat. Acad. Sci. USA*, 87:1874, 1990.
Hallmayer et al., *Am. J. Hum. Genet.*, 77(3):468-76, 2005.
Heinrichs, *Neurosci. Biobehavioral Rev.*, 28(4):379-94, 2004.
Janz et al., *Neuroscience*, 94:1279-1290, 1999.
Kay et al., *Br. J. Psychiatry Suppl.*, 59-67, 1989.
Kay et al., *Schizophr. Bull.*, 13:261-276, 1987.
Kay, *Positive and Negative Syndromes in Schizophrenia*, Routledge, 1991.
Kendler et al., *Am. J. Psychiatry*, 152(5):749-54, 1995.
Klein et al., *Proc. Natl. Acad. Sci. USA*, 96:4494-4499, 1999.
Kwoh et al., *Proc. Natl. Acad. Sci. USA*, 86:1173, 1989.
Landegren et al., *Science*, 241:1077, 1988.
Lazzell et al., *J. Biol. Chem.*, 279:52124-52131, 2004.

Leucht et al., *Mol. Psychiatry*, 14(4):429-47, 2009.
Leucht et al., *Schizophr. Res.*, 79:231-238, 2005.
Lieberman et al., *N. Engl. J. Med.*, 353(12):1209-23, 2005.
Linder et al., *Clin. Chem.*, 43:254-266, 1997.
Mattila et al., *Nucleic Acids Res.*, 19:4967, 1991.
McPherson et al., *PCR Basics: From Background to Bench*, Springer Verlag, 2000.
Meltzer and Bobo, In: *Antipsychotic and Anticholinergic Drugs*, Gelder et al. (Eds.), New Oxford Textbook of Psychiatry, 2nd Ed., Oxford University Press, UK. 2009.
Meltzer, *Int. J. Neuropsychopharmacol.*, 8(2):153-6, 2005.
Myers et al., *Science*, 230:1242, 1985.
Nasrallah, *Acta Psychiatr. Scand.*, 115(4):260-7, 2007.
Nath and Johnson, *Biotechnic. Histochem.*, 73(1):6-22, 1998.
Nielsen et al., *Amer. Chem. Soc.*, 5:1, 1994.
Orita et al., *Proc. Natl. Acad. Sci. USA*, 86:2766-2770, 1989.
*PCR Primer: A Laboratory Manual*, Dieffenbach and Dveksler (Eds.)
PCT Appln. PCT US/93/04145
PCT Appln. WO 92/10092
PCT Appln. WO 95/11995
Perlis et al., *J. Clin. Psychopharmacol.*, 25(5):427-34, 2005.
*Practice Guideline for the Treatment of Patients With Schizophrenia*, American Psychiatric Association, Second Edition, American Psychiatric Association, 2004.
Purcell et al., *Amer. J. Human Genetics*, 81:559-575, 2007.
Raca et al., *Genet. Test.*, 8(4):387-94, 2004.
Redon et al., *Nature*, 444(7118):444-54, 2006.
Saiki et al., *Nature* (London), 324:163-166, 1986.
Sanger et al., *Proc. Natl. Acad. Sci. USA*, 74:5463-5467, 1977.
Schivell et al., *Mol. Cell. Neurosci.*, 29:56-64, 2005.
Sheffield et al., *Proc. Natl. Acad. Sci. USA*, 86:232-236, 1989.
Snijders et al. In: *Bacterial Artificial Chromosomes: Methods and Protocols*, Zhao et al. (eds), Methods in Molecular Biology, Humana Press, 2002.
Snijders et al., *Nat. Genetics*, 29:263-264, 2001.
Stahl and Grady, *Psychiatr. Serv.*, 57(1):127-9, 2006.
Stroup et al., *Schizophr. Bull.*, 29(1):15-31, 2003.
Sullivan et al., *Mol. Psychiatry*, 13(6):570-584, 2008.
Sullivan et al., *Molec. Psychiatry*, http://www.nature.com/mp/journal/v13/n6/suppinfo/mp200825s1.html?url=/mp/journal/v13/n6/abs/mp 200825a.html, 2009.
*Treatment of Patients With Bipolar Disorder*, American Psychiatric Association, 2nd Ed., American Psychiatric Association, 2006.
Underhill et al., *Genome Research*, 7(10):996-1005, 1997
Wheeless et al., *Cytometry*, 17:319-326, 1994.
Wu and Wallace, Genomics, 4:560, 1989.
Xu et al., *Nat. Cell Biol.*, 3:691-698, 2001.
Zobel and Maier, *Nervenarzt.*, 75(3):205-14, 2004.

What is claimed is:

1. A method for treating a human subject having or suspected of having schizophrenia comprising:
   a) selecting a subject having schizophrenia whose genetic material has been tested and determined to contain the OPRP genetic signature, wherein the OPRP genetic signature is defined as a genotype comprising a homozygous genotype for the T allele at rs11960832 and either a homozygous or heterozygous genotype for the T allele at rs7975477, and
   b) treating the subject that was determined not to have the OPRP genetic signature with an anti-psychotic treatment other than olanzapine.

2. The method of claim 1, wherein the anti-psychotic treatment other than olanzapine is risperidone.

3. The method of claim 1, wherein the anti-psychotic treatment other than olanzapine is quetiapine.

4. The method of claim 1, wherein the anti-psychotic treatment other than olanzapine is ziprasidone.

5. The method of claim 1, wherein the anti-psychotic treatment other than olanzapine is perphenzazine.

6. A method for treating a human subject having or suspected of having schizophrenia comprising:
   a) selecting a subject having schizophrenia whose genetic material has been tested and determined not to contain the OPRP genetic signature, wherein the OPRP genetic signature is defined as a genotype comprising a homozygous genotype for the T allele at rs11960832 and either a homozygous or heterozygous genotype for the T allele at rs7975477, and
   b) treating the subject that was determined not to have the OPRP genetic signature with olanzapine.

* * * * *

UNITED STATES PATENT AND TRADEMARK OFFICE
CERTIFICATE OF CORRECTION

PATENT NO.         : 7,932,042 B1
APPLICATION NO.    : 12/903891
DATED              : April 26, 2011
INVENTOR(S)        : Timothy L. Ramsey et al.

It is certified that error appears in the above-identified patent and that said Letters Patent is hereby corrected as shown below:

In claim 1, column 46, line 19, delete "not".

Signed and Sealed this
Ninth Day of August, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,932,042 B1 | Page 1 of 1 |
| APPLICATION NO. | : 12/903891 | |
| DATED | : April 26, 2011 | |
| INVENTOR(S) | : Timothy L. Ramsey et al. | |

It is certified that error appears in the above-identified patent and that said Letters Patent is hereby corrected as shown below:

In the Specifications:

In column 1, lines 7-10, delete
"This invention was made with government support under SBIR grant MH078437 awarded by National Institutes of Mental Health. The government has certain rights in the invention."
and insert
--This invention was made with government support under grant MH078437 awarded by National Institute of Mental Health/National Institutes of Health. The government has certain rights in the invention.-- therefor.

Signed and Sealed this
Fourteenth Day of May, 2013

Teresa Stanek Rea
*Acting Director of the United States Patent and Trademark Office*